United States Patent
Mazela et al.

(10) Patent No.: US 9,592,361 B2
(45) Date of Patent: Mar. 14, 2017

(54) VENTILATION CIRCUIT ADAPTOR AND PROXIMAL AEROSOL DELIVERY SYSTEM

(75) Inventors: Jan Mazela, Poznan (PL); Christopher Henderson, Solana Beach, CA (US)

(73) Assignee: WINDTREE THERAPEUTICS, INC., Warrington, PA (US)

( * ) Notice: Subject to any disclaimer, the term of this patent is extended or adjusted under 35 U.S.C. 154(b) by 1637 days.

(21) Appl. No.: 12/922,981

(22) PCT Filed: Mar. 17, 2009

(86) PCT No.: PCT/US2009/037409
§ 371 (c)(1),
(2), (4) Date: Sep. 16, 2010

(87) PCT Pub. No.: WO2009/117422
PCT Pub. Date: Sep. 24, 2009

(65) Prior Publication Data
US 2011/0011395 A1    Jan. 20, 2011

Related U.S. Application Data

(60) Provisional application No. 61/069,850, filed on Mar. 17, 2008, provisional application No. 61/076,442, filed on Jun. 27, 2008.

(51) Int. Cl.
*A61M 16/14*    (2006.01)
*A61M 16/08*    (2006.01)
(Continued)

(52) U.S. Cl.
CPC ........ *A61M 16/14* (2013.01); *A61M 15/0003* (2014.02); *A61M 16/0057* (2013.01);
(Continued)

(58) Field of Classification Search
USPC ............ 128/208.18, 203.12, 203.25, 205.24
See application file for complete search history.

(56) References Cited

U.S. PATENT DOCUMENTS

| | | |
|---|---|---|
| 2,417,759 A | 3/1947 | Johnson |
| 3,183,906 A | 5/1965 | Moyat |

(Continued)

FOREIGN PATENT DOCUMENTS

| | | |
|---|---|---|
| EP | 0242790 A2 | 10/1987 |
| EP | 0284227 A2 | 9/1988 |

(Continued)

OTHER PUBLICATIONS

Amirav, I., et al., "Nebuliser hood compared to mask in wheezy infants: aerosol therapy without tears," Arch Dis. Child, 2003, 88, 719-723.

(Continued)

*Primary Examiner* — Rachel Young
(74) *Attorney, Agent, or Firm* — Marina E. Volin

(57) ABSTRACT

An adaptor for delivering an aerosolized active agent to a patient with concomitant positive pressure ventilation includes an aerosol flow channel having an aerosol inlet port and a patient interface port, and defining an aerosol flow path from the aerosol inlet port to and through the patient interface port; and a ventilation gas flow channel in fluid communication with the aerosol flow channel and having a gas inlet port and a gas outlet port, and defining a ventilation gas flow path from the gas inlet port to and through the gas outlet port, wherein the ventilation gas flow path is at least partially offset from the aerosol flow path and at least partially encircles the aerosol flow path. Systems and methods for delivering an aerosolized active agent to a patient with concomitant positive pressure ventilation incorporate the adaptor.

9 Claims, 14 Drawing Sheets

(51) Int. Cl.
*A61M 15/00* (2006.01)
*A61M 11/00* (2006.01)
*A61M 16/10* (2006.01)
*A61M 16/20* (2006.01)
*A61M 16/16* (2006.01)
*A61M 16/00* (2006.01)

(52) U.S. Cl.
CPC .... *A61M 16/0816* (2013.01); *A61M 16/0833* (2014.02); *A61M 16/0858* (2014.02); *A61M 16/0883* (2014.02); *A61M 16/147* (2014.02); *A61M 16/208* (2013.01); *A61M 11/005* (2013.01); *A61M 15/00* (2013.01); *A61M 16/1075* (2013.01); *A61M 16/16* (2013.01); *A61M 2016/0027* (2013.01); *A61M 2202/0208* (2013.01); *A61M 2205/3584* (2013.01); *A61M 2206/18* (2013.01)

(56) References Cited

U.S. PATENT DOCUMENTS

| | | | |
|---|---|---|---|
| 3,667,475 | A | 6/1972 | Venturelli et al. |
| 3,842,828 | A * | 10/1974 | Bird ........................ 128/200.14 |
| 4,240,417 | A | 12/1980 | Holever |
| 4,417,574 | A | 11/1983 | Talonn et al. |
| 4,457,305 | A | 7/1984 | Shanks et al. |
| 4,815,459 | A | 3/1989 | Beran |
| 4,828,844 | A | 5/1989 | Rontgen-Odenthal et al. |
| 5,006,343 | A | 4/1991 | Benson et al. |
| 5,044,361 | A | 9/1991 | Werner et al. |
| 5,049,388 | A | 9/1991 | Knight et al. |
| 5,131,387 | A | 7/1992 | French et al. |
| 5,164,369 | A | 11/1992 | Cochrane et al. |
| 5,178,138 | A | 1/1993 | Walstrom et al. |
| 5,228,436 | A | 7/1993 | Parkin |
| 5,230,884 | A | 7/1993 | Evans et al. |
| 5,260,273 | A | 11/1993 | Cochrane et al. |
| 5,262,405 | A | 11/1993 | Girod-Vaquez et al. |
| 5,292,499 | A | 3/1994 | Evans et al. |
| 5,297,543 | A | 3/1994 | Larson et al. |
| 5,299,566 | A | 4/1994 | Davis et al. |
| 5,309,903 | A | 5/1994 | Long |
| 5,320,096 | A | 6/1994 | Hans |
| 5,355,872 | A | 10/1994 | Riggs et al. |
| 5,357,946 | A * | 10/1994 | Kee et al. ................ 128/200.24 |
| 5,407,914 | A | 4/1995 | Cochrane et al. |
| 5,433,195 | A | 7/1995 | Kee et al. |
| 5,471,979 | A | 12/1995 | Psaros et al. |
| 5,474,759 | A | 12/1995 | Fassberg et al. |
| 5,479,920 | A | 1/1996 | Piper et al. |
| 5,546,930 | A | 8/1996 | Wikefeldt |
| 5,590,644 | A | 1/1997 | Rosenkoetter |
| 5,616,158 | A | 4/1997 | Biendarra et al. |
| 5,657,750 | A | 8/1997 | Colman et al. |
| 5,720,282 | A | 2/1998 | Wright |
| 5,743,251 | A | 4/1998 | Howell et al. |
| 5,789,381 | A | 8/1998 | Cochrane et al. |
| 5,829,428 | A | 11/1998 | Walters et al. |
| 5,853,003 | A | 12/1998 | Faithful et al. |
| 5,925,334 | A | 7/1999 | Rubin et al. |
| 6,014,972 | A | 1/2000 | Sladek |
| 6,269,810 | B1 | 8/2001 | Brooker et al. |
| 6,309,623 | B1 | 10/2001 | Weers et al. |
| 6,309,624 | B1 | 10/2001 | Sapsford et al. |
| 6,315,983 | B1 | 11/2001 | Eistetter |
| 6,451,339 | B2 | 9/2002 | Patel et al. |
| 6,494,203 | B1 * | 12/2002 | Palmer ..................... 128/202.27 |
| 6,503,481 | B1 | 1/2003 | Thurston et al. |
| 6,524,557 | B1 | 2/2003 | Backstrom et al. |
| 6,550,476 | B1 | 4/2003 | Ryder |
| 6,572,841 | B1 | 6/2003 | Mautone |
| 6,575,944 | B1 | 6/2003 | McNary et al. |
| 6,579,254 | B1 | 6/2003 | McNary et al. |
| 6,581,600 | B2 | 6/2003 | Bird |
| 6,613,734 | B2 | 9/2003 | Cochrane et al. |
| 6,615,824 | B2 | 9/2003 | Power |
| 6,635,283 | B2 | 10/2003 | Edwards et al. |
| 6,645,467 | B2 | 11/2003 | Mautone |
| 6,660,715 | B2 | 12/2003 | Klibanov |
| 6,737,044 | B1 | 5/2004 | Dickinson et al. |
| 6,770,619 | B2 | 8/2004 | Larsson et al. |
| 6,921,527 | B2 | 7/2005 | Platz et al. |
| 7,040,314 | B2 | 5/2006 | Nguyen et al. |
| 7,201,167 | B2 | 4/2007 | Fink et al. |
| 7,219,668 | B2 * | 5/2007 | Flynn ....................... 128/205.13 |
| 7,360,541 | B2 | 4/2008 | Dhuper et al. |
| 2002/0108614 | A1 * | 8/2002 | Schultz .................... 128/207.14 |
| 2003/0136399 | A1 | 7/2003 | Foley et al. |
| 2004/0011364 | A1 | 1/2004 | Dhuper et al. |
| 2005/0011514 | A1 | 1/2005 | Power et al. |
| 2005/0066964 | A1 | 3/2005 | Bathe |
| 2005/0139211 | A1 | 6/2005 | Alston et al. |
| 2005/0172954 | A1 | 8/2005 | Smith et al. |
| 2005/0178383 | A1 * | 8/2005 | Mackie et al. ........... 128/203.16 |
| 2005/0199236 | A1 | 9/2005 | Fink et al. |
| 2005/0205089 | A1 | 9/2005 | Fink et al. |
| 2005/0217666 | A1 | 10/2005 | Fink et al. |
| 2005/0229926 | A1 | 10/2005 | Fink et al. |
| 2005/0229927 | A1 | 10/2005 | Fink et al. |
| 2005/0229928 | A1 | 10/2005 | Ivri et al. |
| 2006/0078506 | A1 | 4/2006 | Niven et al. |
| 2006/0120968 | A1 | 6/2006 | Niven et al. |
| 2008/0000470 | A1 | 1/2008 | Minocchieri et al. |
| 2008/0017198 | A1 | 1/2008 | Ivri |
| 2008/0264412 | A1 | 10/2008 | Meyer et al. |
| 2009/0025722 | A1 | 1/2009 | Peiper et al. |

FOREIGN PATENT DOCUMENTS

| | | |
|---|---|---|
| EP | 04600731 A1 | 12/1991 |
| EP | 0549266 A2 | 6/1993 |
| EP | 1222940 A2 | 7/2002 |
| FR | 1416169 A | 10/1965 |
| GB | 2272745 A1 | 5/1994 |
| WO | WO0045884 A1 | 8/2000 |
| WO | WO0178819 A1 | 10/2001 |
| WO | WO03013340 A2 | 2/2003 |
| WO | WO03047674 A1 | 6/2003 |
| WO | WO2008028092 A2 | 3/2008 |
| WO | WO2008042912 A2 | 4/2008 |

OTHER PUBLICATIONS

Ballard, J. et al., "A survey of albuterol administration practices in intubated patients in the neonatal intensive care unit," Respiratory Care, 2002, 47)1), 31-38.

Bambang, S., et al., "Surfactant nebulization does not alter airflow obstruction and bronchial responsiveness to histamine in children," Am. J. Respir. Crit. Care Med., 1996, 153, 1148-1152.

Dijk, et al., "Surfactant nebulisation: safety, efficiency and influence on surface owering properties and biochemical composition," Intensive Care Med., 1997, 23, 456-462.

Dubus, J.C., et al., "Aerosol disposition in neonatal ventilation," Pediatric Res., 2005, 58(a), 1-5.

Fink, J.B., et la. "Devide and equipment evaluations," Respir. Care, 2004, 49(10), 1157-1164.

Fink, J.B., et al., "Aerosol delivery to ventilation infant and pediatric patients," Respir. Care, 2004, 49(6), 653-665.

Geller, D.E., et al., "Efficiency of pulmonary administration of tobramycin solution for inhalation in cystic fibrosis using an improved drug delivery system," Chest, 2003, 123, 28-36.

Glasser, S.W., et al., "cDNA and deduced amino acid sequence of human pulmonary surfactant-associated proteolipid SPL(Phe)," Proc. Natl. Acad. Sci., 1987, 84, 4007-4011.

Hopp, T.P., et al., "Prediction of protein antigenic determinants from amino acid sequences," PRoc. Natl. Acad. Sci. USA, 1981, 78(6), 3824-3828.

Kattwinkel, J., et al., "Technique for intrapartum admininistration of surfactant without requirement for an endotracheal tube," J. of Pern.

(56) References Cited

OTHER PUBLICATIONS

Ma, et al., "Effects of a cationic and hydrophobic peptide, KL4, on model lung surfactant lipid monolayers," Biophysical J., 1998, 74, 1899-1907.

Rosenfeld, W.N., et al., "Water intoxication: a complication of nebulization with nasal CPAP," J. of Pediatrics, 1976, 89(1), 113-114.

Smedsas-Lofvenberg, A., et al., "Nebulization of drugs in a nasal CPAP system," Acta Paediatr., 1999, 88, 89-92.

Berggren, Acta Paediatr, Pilot study of nebulized surfactant therapy for neonatal respiratory distress syndrome, 2000, 89:460-464.

Cheifetz, I.M., Respiratory Care, Invasive and Noninvasive Pediatric Mechanical Ventilation, 2004, 48:442-458.

T.T. Nguyen, K.A., Cox, M. Parker and S. Pham (2003) Generation and Characterization of Soft-Mist Aerosols from Aqueous Formulations Using the Capillary Aerosol Generator, J. Aerosol Med., 16:189.

Kattwinkel, J., et al., Technique for intrapartum administration of surfactant without requirement for an endotracheal tube, J Perinatology, 2004, p. 1-6.

Trevisanuto, E., et al. Laryngeal mask airway used as a delivery conduit for the administration of surfactant to preterm infants with respiratory distress syndrome, Biol Neonate, 2005, 87(4): p. 217-220.

Richardson, C. and A. Jung, Effect of continuous positive airway pressure on pulmonary function and blood gases of infants with respiratory distress syndrome, Pediat. Res., 1978, 12: p. 771-774.

Gaon, P., et al., Assessment of effect of nasal continuous positive pressure on laryngeal opening using fibre optic laryngoscopy, Arch Dis Child Fetal Neonatal Ed. 1999, 80(3), pp. F230-F232.

Thomson, M., et al., Treatment of immature baboons for 28 days with early nasal continuous positive airway pressure, Am J Respir Crit Care Med, 2004, 160(9): p. 1054-1062.

Verder, H., et al., Surfactant therapy and nasal continuous positive airway pressure for newborns with respiratory distress syndrome, Danish-Swedish Multicenter Study Group, N Engl J Med, 1994, 331(16): p. 1051-1055.

Verder, H., et al. Nasal continuous positive airway pressure and early surfactant therapy for respiratory distress syndrome in newborns of less than 30 weeks' gestation, Pediatrics, 1999, 103(2): p. 1-6.

Dolovich, M., Influence of inspiratory flow rate, particle size, and airway caliber on aerosolized drug delivery to the lung, Respiratory Care, 2000, 45(6): p. 597-608.

Becquemin, M., et al., Particle deposition and resistance in the noses of adults and children, Eur Respir J, 1991, 4:p. 694-702.

Salmon, B., N. Wilson, and M. Silverman, How much aerosol reaches the lungs of wheezy infants and toddlers? Archives of Disease in Childhood, 1990, 65: p. 401-403.

Fink, J.B., et al., Can high efficiency aerosol delivery continue after extubation? Critical Care, 2005, 9(Suppl1): p. P129.

Beck, J. et al., Prolonged neural expiratory time induced by mechanical ventilation in infants, Pediatric Research, 2004, 55(5): p. 747-754.

International Preliminary Report on Patentability for PCT Application No. PCT/US2009/037409, dated Sep. 20, 2010.

International Search Report and Written Opinion corresponding to PCT Application No. PCT/US2009/037409, dated May 12, 2009.

Foust, G.N., et al., "Shortcomings of using two jet nebulizers in tandem with an aerosol face mask for optimal oxygen therapy," Chest, 1991;99;1346-1351.

Kattwinkel, J., et al., "Technique for intrapartum admininistration of surfactant without requirement for an endotracheal tube," Journal of Perinatology, 2004; 24:360-365.

\* cited by examiner

VENTILATION CIRCUIT ADAPTOR AND PROXIMAL AEROSOL DELIVERY SYSTEM

CROSS-REFERENCE TO RELATED APPLICATIONS

This application claims the benefit of provisional Application Nos. 61/069,850, filed Mar. 17, 2008, titled VENTILATION CIRCUIT ADAPTOR and 61/076,442, filed Jun. 27, 2008, titled VENTILATION CIRCUIT ADAPTOR AND PROXIMAL AEROSOL DELIVERY SYSTEM, which are incorporated herein in their entirety.

BACKGROUND OF THE INVENTION

1. Field of Invention

This invention relates to pulmonary therapy and ventilatory support of pulmonary function. In particular, the invention is directed to an aerosol delivery system and a ventilation circuit adaptor for pulmonary delivery of aerosolized substances and/or for other therapeutic and/or diagnostic purposes, in combination with noninvasive or invasive respiratory ventilation support.

2. Description of Related Art

Various patents, patent publications and scientific articles may be referred to throughout the specification. The contents of each of these documents are incorporated by reference herein, in their entireties.

Patients, both adult and infants, in respiratory failure or those with respiratory dysfunction are typically mechanically ventilated in order to provide suitable rescue and prophylactic therapy. Respiratory failure in adults or infants can be caused by any condition relating to poor breathing, muscle weakness, abnormality of lung tissue, abnormality of the chest wall, and the like. Additionally, pre- and full-term infants born with a respiratory dysfunction, such as respiratory distress syndrome (RDS), meconium aspiration syndrome (MAS), persistent pulmonary hypertension (PPHN), acute respiratory distress syndrome (ARDS), pheumocystis carinii pneumonia (PCP), transient tachypnea of the newborn (TTN) and the like often require prophylactic or rescue respiratory support. In addition to respiratory support, infants suffering from, or at risk of RDS are often treated with exogenous surfactant, which improves gas exchange and has had a dramatic impact on mortality. Typically, the exogenous material is delivered as a liquid bolus to the central airways via a catheter introduced through an endotracheal tube. Infants born at 28 weeks or less are almost universally intubated and mechanically ventilated. There is a significant risk of failure during the process of intubation and a finite chance of causing damage to the upper trachea, laryngeal folds and surrounding tissue. Mechanical ventilation over a prolonged time, particularly where elevated oxygen tensions are employed, can also lead to acute lung damage. If ventilation and oxygen is required for prolonged periods of time and/or if the ventilator is not sufficiently managed, the clinical consequences can include bronchopulmonary dysplasia, chronic lung disease, pulmonary hemorrhage, intraventricular hemorrhage, and periventricular leukomalacia.

Infants born of larger weight or gestational age who are not overtly at risk of developing respiratory distress syndrome, or infants who have completed treatment for respiratory distress syndrome can be supported by noninvasive means. Attempts were made to administer liquid surfactant without intubation: to the posterior pharynx through the catheter, with spontaneously breathing infant [1], or to the pharynx through the laryngeal mask with transient positive pressure ventilation (PPV) [2]. Another non-invasive approach is nasal continuous positive airway pressure ventilation (nCPAP or CPAP). CPAP is a means to provide voluntary ventilator support while avoiding the invasive procedure of intubation. Nasal CPAP is widely accepted among clinicians as a less invasive mode of ventilatory support for preterm newborns with mild/moderate RDS. CPAP has been demonstrated to be effective in increasing functional residual capacity (FRC) by stabilizing and improving alveolar function [3], and in dilating the larynx [4]. Based on animal work, CPAP in combination with surfactant therapy has been also shown to minimize the risk for bronchopulmonary dysplasia (BPD) development among preterm baboons [5]. Randomized clinical trials focused on the use of nCPAP in the prophylaxis of RDS did show the benefit of nCPAP after instillation of surfactant via endotracheal tube [6, 7]. CPAP provides humidified and slightly over-pressurized gas (approximately 5 cm $H_2O$ above atmospheric pressure) to an infant's nasal passageway utilizing nasal prongs or a tight fitting nasal mask. CPAP also has the potential to provide successful treatment for adults with various disorders including chronic obstructive pulmonary disease (COPD), sleep apnea, acute lung injury (ALI)/ARDS and the like.

A typical ventilatory circuit for administering positive pressure ventilation includes a positive pressure generator connected by tubing to a patient interface, such as a mask, nasal prongs, or an endotracheal tube, and an exhalation path, such as tubing that allows discharge of the expired gases, e.g., to the ventilator or to an underwater receptacle as for "bubble" CPAP. The inspiratory and expiratory tubes are typically connected to the patient interface via a "Y" connector, which contains a port for attaching each of the inspiratory and expiratory tubes, as well as a port for the patient interface and, typically, a port for attaching a pressure sensor. In a closed system, such as with use of a tight-fitting mask or endotracheal tube, administration of other pulmonary treatment, e.g., pulmonary surfactant, or diagnosis generally requires temporary disconnection of the ventilatory support while the pulmonary treatment is administered or the diagnosis is conducted.

Recent efforts have focused on delivery of surfactant and/or other active agents in an aerosolized form, in order to enhance delivery and/or avoid or minimize the trauma of prolonged invasive mechanical ventilation. However, if the patient is receiving ongoing ventilatory support, administration of aerosolized active agents may necessitate interruption of the ventilatory support while the aerosol is administered. As a result, attempts have been made to deliver aerosolized active agents simultaneously with noninvasive positive pressure. For instance, Berggren et al. (*Acta Pcediatr.* 2000, 89:460-464) attempted to delivery pulmonary surfactant simultaneously with CPAP, but were unsuccessful due to the lack of sufficient quantities of surfactant reaching the lungs.

U.S. Patent publication 2006/0120968 by Niven et al. describes the concomitant delivery of positive pressure ventilation and active aerosolized agents, including pulmonary surfactants. Delivery was reported to be accomplished through the use of a device and system that was designed to improve the flow and direction of aerosols to the patient interface while substantially avoiding dilution by the ventilation gas stream. The system employed an aerosol conditioning chamber and a uniquely-shaped connector for directing the aerosol and the ventilation gas.

U.S. Pat. No. 7,201,167 to Fink et al., describes a method of treating a disease involving surfactant deficiency or dysfunction by providing aerosolized lung surfactant composition into the gas flow within a CPAP system. As shown in FIGS. 1 and 6 of the Fink et al. patent, the aerosol is carried by air coming from a flow generator wherein the aerosol is being diluted with the air.

Typically, a constant flow CPAP/ventilator circuit used for breathing support consists of an inspiratory arm, a patient interface, an expiratory arm and a source of positive end expiratory pressure (PEEP valve or column of water). Currently, aerosol generator manufacturers place nebulizers within the inspiratory arm of the CPAP/ventilator tubing circuit. This can potentially lead to aerosol dilution and decrease in aerosol concentration (see U.S. Pat. No. 7,201,167 to Fink et al.). Aerosol dilution is caused by much higher flows in the CPAP/ventilator circuit as compared to the peak inspiratory flow (PIF) of treated patients. Placement of the nebulizer between 'Y' connector and endotracheal tube (ET) or other patient interface as proposed by Fink et al. [11] account for significant increase in dead space depraving patient from appropriate ventilation.

To overcome the deficiencies of the prior art, the inventors developed a special adaptor which enables sufficient separation of the aerosol flow from the ventilation flow maintaining optimized ventilation as well as a novel aerosol delivery system.

All references cited herein are incorporated herein by reference in their entireties.

BRIEF SUMMARY OF THE INVENTION

One aspect of the invention features a respiratory ventilation adaptor useful for delivery of an aerosolized active agent to a patient with concomitant positive pressure ventilation. The adaptor comprises: (a) an aerosol flow channel comprising an aerosol inlet port and a patient interface port, and defining an aerosol flow path from the aerosol inlet port to and through the patient interface port; and (b) a ventilation gas flow channel in fluid communication with the aerosol flow channel, comprising a gas inlet port and a gas outlet port, and defining a ventilation gas flow path from the gas inlet port to and through the gas outlet port; wherein the ventilation gas flow path is at least partially offset from the aerosol flow path and at least partially encircles the aerosol flow path.

The adaptor can further comprise a pressure sensor port. The adaptor may also further comprise a valve at the aerosol inlet port. In one embodiment, the valve is a slit or cross-slit valve. In various embodiments, the valve is sufficiently flexible to allow introduction of instruments, catheters, tubes, or fibers into and through the aerosol flow channel and the patient interface port, while maintaining positive ventilatory pressure. The adaptor may also further comprise a removable cap covering the aerosol inlet port. The adaptor may further comprise a one-way valve at the aerosol outlet port.

In certain embodiments, the aerosol flow channel defines a substantially straight aerosol flow path, whereas in other embodiments, the aerosol flow channel defines a curved or angled aerosol flow path. The aerosol flow channel is of substantially the same cross-sectional area throughout its length, or it can be of greater cross sectional area at the aerosol inlet port than it is at the patient interface port. In certain embodiments, the fluid communication between the aerosol flow channel and the ventilation gas flow channel can be provided by an aperture.

In certain embodiments, the ventilation gas flow channel is adapted to form a chamber that includes the gas inlet port, the gas outlet port and the patient interface port, wherein the aerosol flow channel is contained within the chamber and extends from the aerosol inlet port at one end of the chamber, through the chamber to an aerosol outlet port within the chamber and recessed from the patient interface port at the opposite end of the chamber, wherein the aerosol flow channel is of sufficient length to extend beyond the gas inlet and outlet ports. In particular embodiments the aerosol outlet port is recessed from the patient interface port by about 8 millimeters or more. In other particular embodiments, the volume within the chamber between the aerosol outlet port and the patient interface port is about 1.4 milliliters or more.

Another aspect of the invention features a system for delivery of an aerosolized active agent to a patient with concomitant positive pressure ventilation, the system comprising: (a) a positive pressure ventilation circuit comprising a positive pressure generator for producing pressurized ventilation gas and a delivery means for delivering the pressurized ventilation gas to the patient and for directing exhalation gases from the patient; (b) an aerosol generator for producing the aerosolized active agent; and (c) a patient interface for delivering the ventilation gas and the aerosolized active agent to the patient; wherein the positive pressure ventilation circuit and the aerosol generator are connected to the patient interface through a respiratory ventilation adaptor comprising: (i) an aerosol flow channel having an aerosol inlet port and a patient interface port, and defining an aerosol flow path from the aerosol inlet port to and through the patient interface port; and (ii) a ventilation gas flow channel in fluid communication with the aerosol flow channel, comprising a gas inlet port and a gas outlet port, and defining a ventilation gas flow path from the gas inlet port to an through the gas outlet port; wherein the ventilation gas flow path is at least partially offset from the aerosol flow path and at least partially encircles the aerosol flow path.

The adaptor may further comprise a pressure sensor port connected to a pressure sensor, as well as a valve at the aerosol inlet port. In embodiments of the system, connection of the aerosol generator to the adaptor causes the valve to open, and disconnection of the aerosol generator from the adaptor causes the valve to close. In certain embodiments, the valve, when closed, is sufficiently flexible to allow introduction of instruments, catheters, tubes, or fibers into and through the aerosol flow channel and the patient interface port, while maintaining positive ventilatory pressure. The system may further comprise an adaptor with a removable cap for the aerosol inlet port, for use when the aerosol generator is disconnected from the adaptor. In certain embodiments, the patient interface is not invasive, e.g., is a mask or nasal prongs. In other embodiments, the patient interface is invasive, e.g., an endotracheal tube.

Another aspect of the invention relates to a system for delivery of a propelled aerosolized active agent with concomitant positive pressure ventilation to a patient in need of pulmonary lung surfactant, the system comprising: a) a positive pressure ventilation circuit comprising a positive pressure generator for producing pressurized ventilation gas and a delivery conduit for delivering the pressurized ventilation gas to the patient and for directing exhalation gases from the patient; b) an aerosol generator for producing an aerosolized active agent; c) a patient interface for delivering the ventilation gas and the aerosolized active agent to the patient; d) a respiratory ventilation adaptor in communication with the positive pressure ventilation circuit, the aerosol generator and the patient interface; e) an aerosol entrainment chamber to produce the propelled aerosolized active agent, wherein the aerosol entrainment chamber is in communication with the aerosol generator; and f) an auxiliary circuit in connection with the delivery conduit for delivering the pressurized ventilation gas to the patient, wherein the auxiliary circuit comprises a first auxiliary conduit connecting the delivery conduit and the aerosol entrainment chamber and a second auxiliary conduit connecting the aerosol entrainment chamber and the respiratory ventilation adaptor, wherein the first auxiliary conduit is adapted to accommodate a portion of the pressurized ventilation gas which is removed from a main flow of the pressurized ventilation gas directed toward the respiratory ventilation adaptor, and to enable delivery of the portion of the pressurized ventilation gas to the aerosol entrainment chamber for combining with the aerosolized active agent to form the propelled aerosolized active agent and the second auxiliary conduit is adapted to enable delivery of the propelled aerosolized active agent to the respiratory ventilation adaptor.

Yet another aspect of the invention relates to a method of delivery of a propelled aerosolized active agent with concomitant positive pressure ventilation to a patient, the method comprising: a) providing a positive pressure ventilation circuit comprising a positive pressure generator for producing pressurized ventilation gas and a delivery conduit for delivering the pressurized ventilation gas to the patient and for directing exhalation gases from the patient; b) providing an aerosol generator for producing an aerosolized active agent; c) providing a patient interface for delivering the ventilation gas and the aerosolized active agent to the patient; d) providing a respiratory ventilation adaptor in communication with the positive pressure ventilation circuit, the aerosol generator and the patient interface; e) providing an aerosol entrainment chamber in communication with the aerosol generator; providing an auxiliary circuit in connection with the delivery conduit for delivering the pressurized ventilation gas to the patient, wherein the auxiliary circuit comprises a first auxiliary conduit connecting the delivery conduit and the aerosol entrainment chamber and a second auxiliary conduit connecting the aerosol entrainment chamber and the respiratory ventilation adaptor; g) removing a portion of the pressurized ventilation gas from a main flow of the pressurized ventilation gas directed toward the respiratory ventilation adaptor to the first auxiliary conduit and directing the portion of the pressurized ventilation gas to the aerosol entrainment chamber and thereby combining the portion with the aerosolized active agent to form a propelled aerosolized active agent; h) directing the propelled aerosolized active agent to the second auxiliary conduit and thereby deliver the propelled aerosolized active agent to the respiratory ventilation adaptor; and i) providing the propelled aerosolized active agent and the pressurized ventilation gas to the patient interface and thereby deliver the ventilation gas and the propelled aerosolized active agent to the patient.

Yet another aspect of the invention is an improvement to a method of delivery of an aerosolized active agent with concomitant positive pressure ventilation to a patient in need of pulmonary lung surfactant, the improvement comprising diverting a portion of pressurized ventilation gas directed to the patient to be combined with a concentrated aerosolized active agent in a chamber and using the portion of the pressurized ventilation gas as a carrier (sheath) gas for delivery of the aerosolized active agent to the patient.

Yet another aspect of the invention is a method for delivering an aerosolized active agent to a patient with concomitant positive pressure ventilation, the method comprising: a) providing a positive pressure ventilation circuit comprising a positive pressure generator for producing a pressurized ventilation gas and a delivery conduit for delivering an amount of the pressurized ventilation gas to the patient and for directing a flow of exhalation gas from the patient; b) providing an aerosol generator for producing the aerosolized active agent; c) providing a patient interface for delivering the ventilation gas, the aerosolized active agent or the mixture thereof to the patient; d) connecting the positive pressure ventilation circuit and the aerosol generator to the patient interface through an adaptor, the adaptor comprising: i) an aerosol flow channel having an aerosol inlet port and a patient interface port, and defining an aerosol flow path from the aerosol inlet port to and through the patient interface port; and ii) a ventilation gas flow channel in fluid communication with the aerosol flow channel and having a gas inlet port and a gas outlet port, and defining a ventilation gas flow path from the gas inlet port to and through the gas outlet port, wherein the ventilation gas flow path is at least partially offset from the aerosol flow path and at least partially encircles the aerosol flow path; e) providing the pressurized ventilation gas to the patient, wherein the volume of the pressurized ventilation gas is regulated by at least one of the length of the aerosol flow channel and the pressure created by an increased demand for air which is not matched by the aerosol flow; and f) providing an aerosol flow of the aerosolized active agent to a chamber inside the adaptor such that aerosol flow is introduced below the ventilation gas flow channel wherein the aerosol flow is selected to match the patient's inspiratory flow and thereby providing the aerosolized active agent to the patient. Other features and advantages of the invention will be understood by reference to the drawings, detailed description and examples that follow.

DETAILED DESCRIPTION OF PREFERRED EMBODIMENTS OF THE INVENTION

Figure 1A:
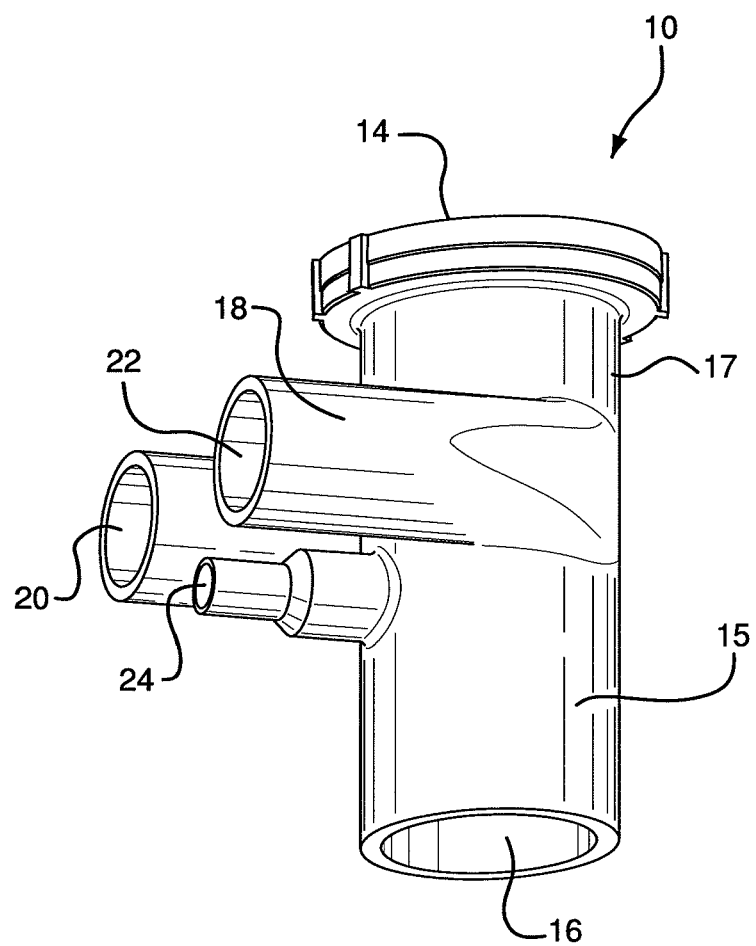
FIG. 1A is an isometric view of an embodiment of the adaptor of the present invention.

The present invention provides, inter alia, devices and systems for pulmonary delivery of one or more aerosolized active agents to a patient, concomitantly with administration of noninvasive or invasive ventilatory support.

Unless otherwise indicated the terminology used herein is for the purpose of describing particular embodiments only and is not intended to limit the scope of the present invention. It must be noted that as used herein and in the claims, the singular forms "a," "and" and "the" include plural referents unless the context clearly dictates otherwise.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "active agent" as used herein refers to a substance or combination of substances or devices that can be used for therapeutic purposes (e.g., a drug), diagnostic purposes or prophylactic purposes via pulmonary delivery. For example, an active agent can be useful for diagnosing the presence or absence of a disease or a condition in a patient and/or for the treatment of a disease or condition in a patient. Certain "active agents" are substances or combinations of substances that are capable of exerting a biological effect when delivered by pulmonary routes. The bioactive agents can be neutral, positively or negatively charged. Exemplary agents include, for example, insulins, autocoids, antimicrobials, antipyretics, antiinflammatories, surfactants, antibodies, antifungals, antibacterials, analgesics, anorectics, antiarthritics, antispasmodics, antidepressants, antipsychotics, antiepileptics, antimalarials, antiprotozoals, antigout agents, tranquilizers, anxiolytics, narcotic antagonists, antiparkinsonisms, cholinergic agonists, antithyroid agents, antioxidants, antineoplastics, antivirals, appetite suppressants, antiemetics, anticholinergics, antihistaminics, antimigraines, bone modulating agents, bronchodilators and antiasthma drugs, chelators, antidotes and antagonists, contrast media, corticosteroids, mucolytics, cough suppressants and nasal decongestants, lipid regulating drugs, general anesthetics, local anesthetics, muscle relaxants, nutritional agents, parasympathomimetics, prostaglandins, radio-pharmaceuticals, diuretics, antiarrhythmics, antiemetics, immunomodulators, hematopoietics, anticoagulants and thrombolytics, coronary, cerebral or peripheral vasodilators, hormones, contraceptives, diuretics, antihypertensives, cardiovascular agents such as cardiotonic agents, narcotics, vitamins, vaccines, and the like.

In one embodiment, the active agent employed is a high-dose therapeutic. Such high dose therapeutics would include antibiotics, such as amikacin, gentamicin, colistin, tobramycin, amphotericin B. Others would include mucolytic agents such as N-acetylcysteine, Nacystelyn, alginase, mercaptoethanol and the like. Antiviral agents such as ribavirin, gancyclovir, and the like, diamidines such as pentamidine and the like and proteins such as antibodies are also contemplated.

A preferred active agent is a substance or combination of substances that is used for pulmonary prophylactic or rescue therapy, such as a pulmonary surfactant (PS).

Natural PS lines the alveolar epithelium of mature mammalian lungs. Natural PS has been described as a "lipoprotein complex" because it contains both phospholipids and apoproteins that act in conjunction to modulate the surface tension at the lung air-liquid interface and stabilize the alveoli to prevent their collapse. Four proteins have been found to be associated with pulmonary surfactant, namely SP-A, SP-B, SP-C, and SP-D (Ma et al., *Biophysical Journal* 1998, 74:1899-1907). Specifically, SP-B appears to impart the full biophysical properties of pulmonary surfactant when associated with the appropriate lung lipids. An absence of SP-B is associated with respiratory failure at birth. SP-A, SP-B, SP-C, and SP-D are cationic peptides that can be derived from animal sources or synthetically. When an animal-derived surfactant is employed, the PS is often bovine or porcine derived.

For use herein, the term PS refers to both naturally occurring and synthetic pulmonary surfactant. Synthetic PS, as used herein, refers to both protein-free pulmonary surfactants and pulmonary surfactants comprising synthetic peptides or peptide mimetics of naturally occurring surfactant protein. Any PS currently in use, or hereafter developed for use in RDS and other pulmonary conditions, is suitable for use in the present invention. Exemplary PS products include, but are not limited to, lucinactant (Surfaxin®, Discovery Laboratories, Inc., Warrington, Pa.), poractant alfa (Curosurf®, Chiesi Farmaceutici SpA, Parma, Italy), beractant (Survanta®, Abbott Laboratories, Inc., Abbott Park, Ill.) and colfosceril palmitate (Exosurf®, GlaxoSmithKline, PLC, Middlesex, U.K.).

While the methods and systems of this invention contemplate use of active agents, such as pulmonary surfactant compositions, antibiotics, antivirals, mucolytic agents, as described above, the preferred active agent is a synthetic pulmonary surfactant. From a pharmacological point of view, the optimal exogenous PS to use in the treatment would be completely synthesized in the laboratory. In this regard, one mimetic of SP-B that has found to be useful is KL4, which is a 21 amino acid cationic peptide. Specifically the KL4 peptide enables rapid surface tension modulation and helps stabilize compressed phospholipid monolayers. KL4 is representative of a family of PS mimetic peptides which are described for example in U.S. Pat. Nos. 5,260,273 and 5,407,914. Preferably, the peptide is present within an aqueous dispersion of phospholipids and free fatty acids or fatty alcohols, e.g., DPPC (dipalmitoyl phosphatidylcholine) and POPG (palmitoyl-oleyl phosphatidylglycerol) and palmitic acid (PA). See, for example, U.S. Pat. No. 5,789,381.

As used herein, the term "aerosol" refers to liquid or solid particles that are suspended in a gas. Typically, the "aerosol" or "aerosolized agent" referred to herein contains one or more of the active agents, as referred to above. The aerosol can be in the form of a solution, suspension, emulsion, powder, solid, or semi-solid preparation.

The term "ventilation" or "respiratory ventilation" as used herein refers to mechanical or artificial support of a patient's breathing. The principles of mechanical ventilation are governed by the Equation of Motion, which states that the amount of pressure required to inflate the lungs depends upon resistance, compliance, tidal volume and inspiratory flow. The principles of mechanical ventilation are described in detail in Hess and Kacmarek, ESSENTIALS OF MECHANICAL VENTILATION, $2^{nd}$ Edition, McGraw-Hill Companies (2002). The overall goals of mechanical ventilation are to optimize gas exchange, patient work of breathing and patient comfort while minimizing ventilator-induced lung injury. Mechanical ventilation can be delivered via positive-pressure breaths or negative-pressure breaths. Additionally, the positive-pressure breaths can be delivered noninvasively or invasively.

Noninvasive mechanical ventilation (NIMV) generally refers to the use of a mask or nasal prongs to provide ventilatory support through a patient's nose and/or mouth. The most commonly used interfaces for noninvasive positive pressure ventilation are nasal prongs, nasopharyngeal tubes, masks, or oronasal masks. Desirable features of a mask for noninvasive ventilation include low dead space, transparent, lightweight, easy to secure, adequate seal with low facial pressure, disposable or easy to clean, nonirritating to the skin (non-allergenic) and inexpensive.

NIMV is distinguished from those invasive mechanical ventilatory techniques that bypass the patient's upper airway with an artificial airway (endotracheal tube, laryngeal mask airway or tracheostomy tube). NIMV can be provided by either bi-level pressure support (so called "BI-PAP") or continuous positive airway pressure (CPAP). Bi-level support provides an inspiratory positive airway pressure for ventilatory assistance and lung recruitment, and an expiratory positive airway pressure to help recruit lung volume and, more importantly, to maintain adequate lung expansion. Continuous positive airway pressure provides a single level of airway pressure, which is maintained above atmospheric pressure throughout the respiratory cycle. For a further review of invasive and noninvasive mechanical ventilation, see Cheifetz, I. M., *Respiratory Care,* 2003, 48:442-453.

The employment of mechanical ventilation, whether invasive or non-invasive, involves the use of various respiratory gases, as would be appreciated by the skilled artisan. Respiratory gases pulmonary respiratory therapy are sometimes referred to herein as "CPAP gas," "ventilation gas," "ventilation air," or simply "air." However, those terms are intended to include any type of gas normally used for respiratory therapy. The terms "channel" and "chamber" are used interchangeably in this disclosure and are not intended to be limited to any particular shape or form.

The term "a delivery means" when used together with ventilation gas refer to a conduit or a network of conduits containing (if needed) various devices (pressure valves, sensors, etc.) necessary to enable delivery of ventilation gas, preferably pressurized ventilation gas, to and from the adaptor. The type of conduits, their geometry and materials they are made of are not limited to any specifics. A person skilled in the art should be able to select appropriate conduits and devices based on the teaching disclosed herein and knowledge available in the art.

Turning now to the drawings, FIG. 1A shows an embodiment of the ventilation circuit adaptor 10 including a body 15, an aerosol flow chamber 17 and a ventilation gas flow chamber 18. The aerosol flow chamber 17 comprises an aerosol inlet port 14 with an optional valve (not visible) and a patient interface port 16. As shown in FIG. 2B, aerosol is passed from an aerosol generator (not shown) directly or indirectly (e.g., via tubing) through the aerosol inlet port 14 into the aerosol flow channel 12 and out of the aerosol flow channel 12 to the patient via the aerosol outlet port 30 to and through the patient interface port 16. The patient interface port 16 is connected directly or indirectly (e.g., via tubing) to a patient interface, such as an endotracheal tube, a mask or nasal prongs (not shown). As shown in FIG. 1A, the ventilation gas flow chamber 18 comprises ventilation gas inlet and outlet ports 20 and 22, respectively. It is understood that the inlet and the outlet can be switched such that the inlet can become an outlet and the outlet can become the inlet. In this embodiment, the ventilation gas flow chamber 18 is joined with the aerosol flow chamber 17 to facilitate flow of the aerosol without dilution with ventilation gas or with a minimum dilution as shown more fully in FIGS. 2A-4. The body 15 further comprises an optional pressure sensor port 24. While the main body of the adaptor 10 is preferably roughly cylindrical along its length, it will be appreciated by one of skill in the art that the body of the adaptor 10 may utilize any cross-sectional shape.

Figure 1C:
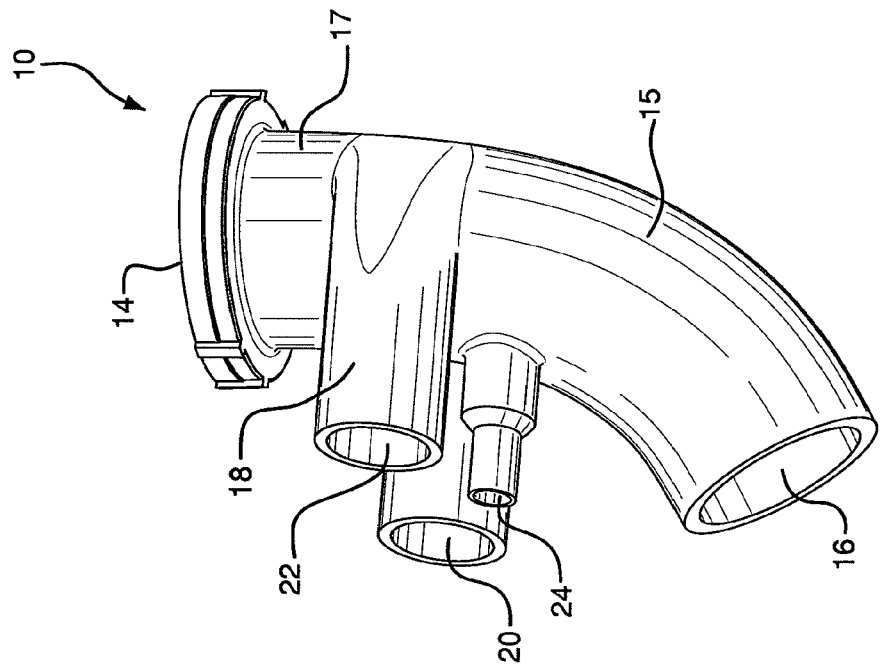
FIGS. 1B and 1C are isometric views of alternative embodiments of the adaptor.
Figure 1B:
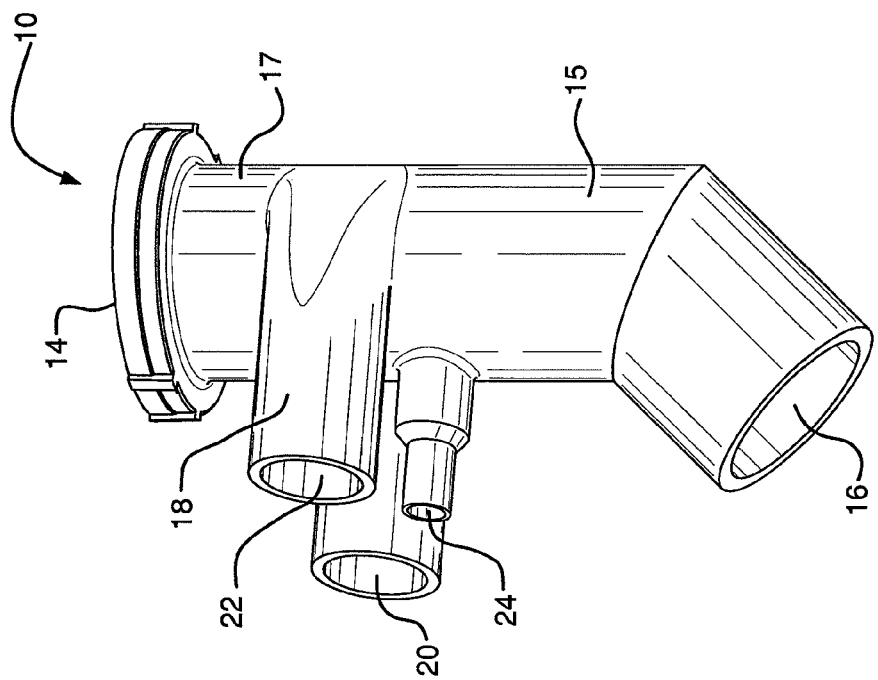

FIGS. 1B and 1C illustrate alternative embodiments of the adaptor shown in FIG. 1A. FIG. 1B shows an angled configuration; FIG. 1C shows a curved configuration.

Figure 2A:
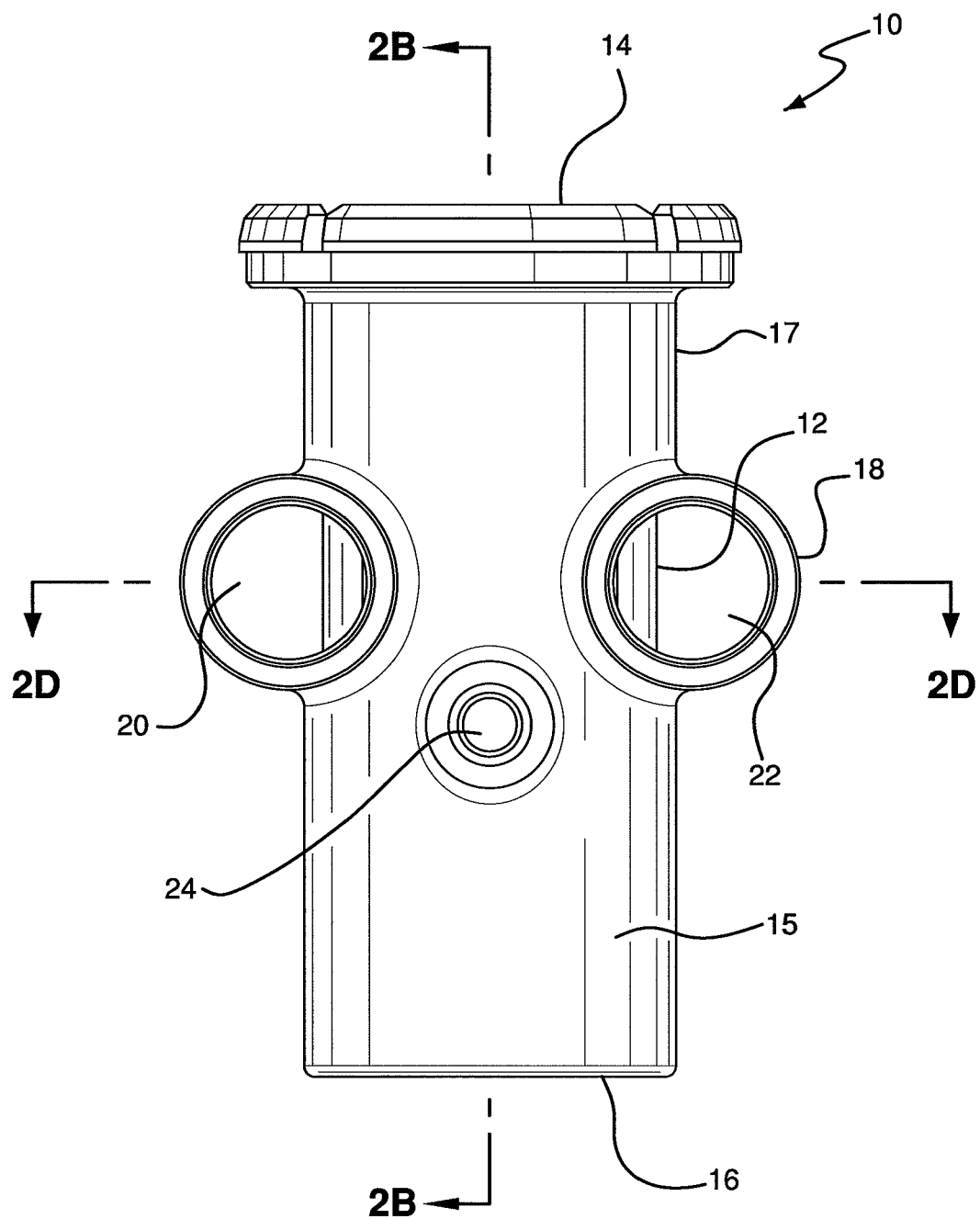
FIG. 2A is a plan view of the front of the adaptor of FIG. 1A.
Figure 2B:
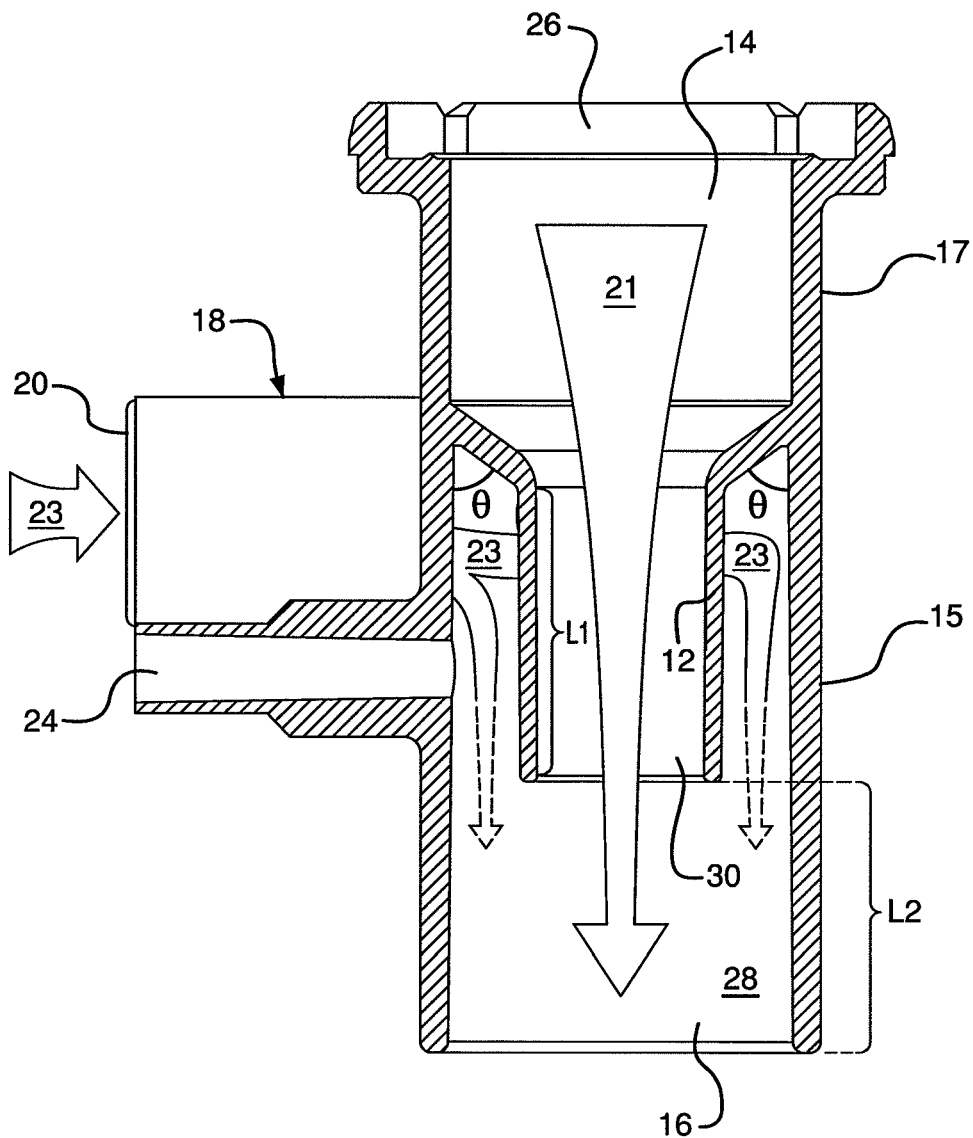
FIG. 2B is a section view of the adaptor of FIG. 2A, as seen along line 2B-2B.
Figure 2C:
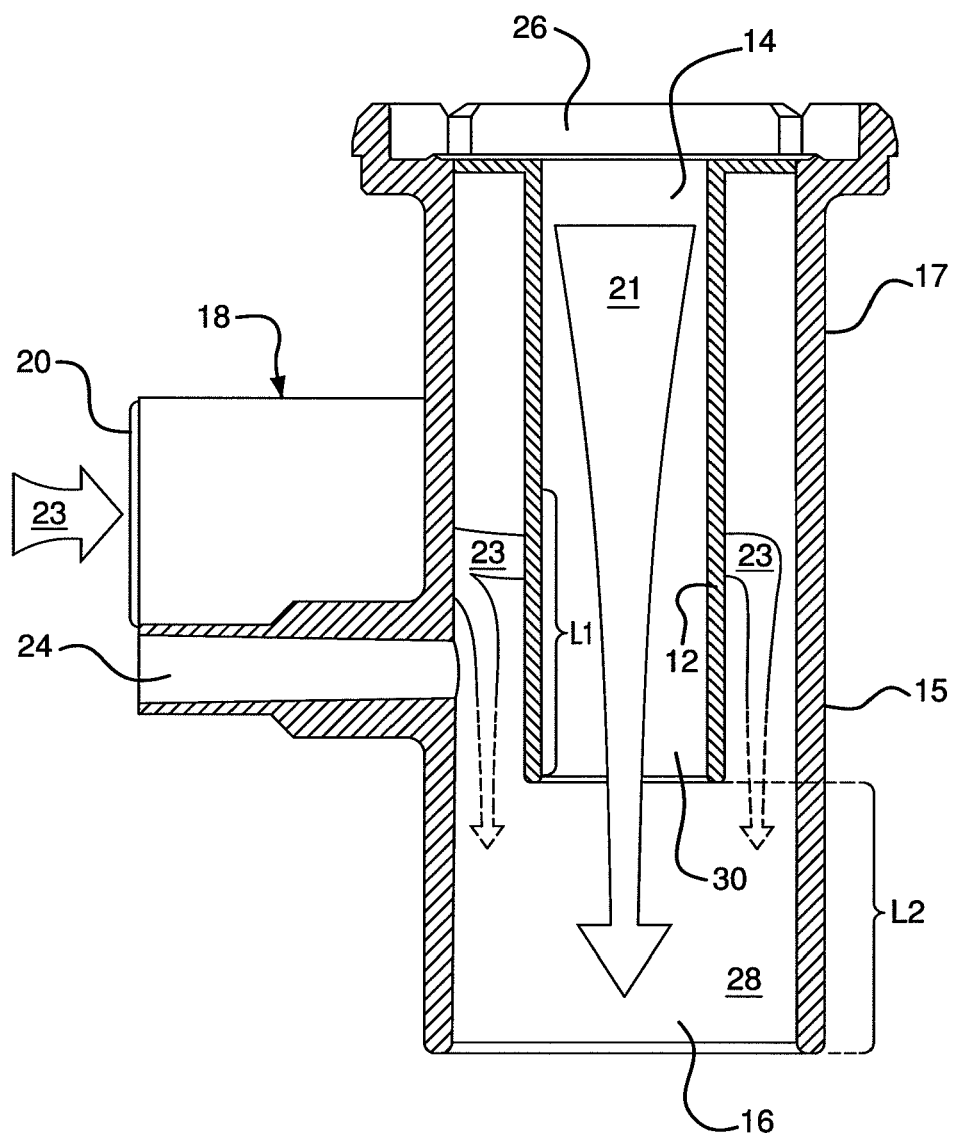
FIG. 2C is a section view of the adaptor of FIG. 2A as seen along line 2B-2B, showing an alternative internal configuration.
Figure 4:
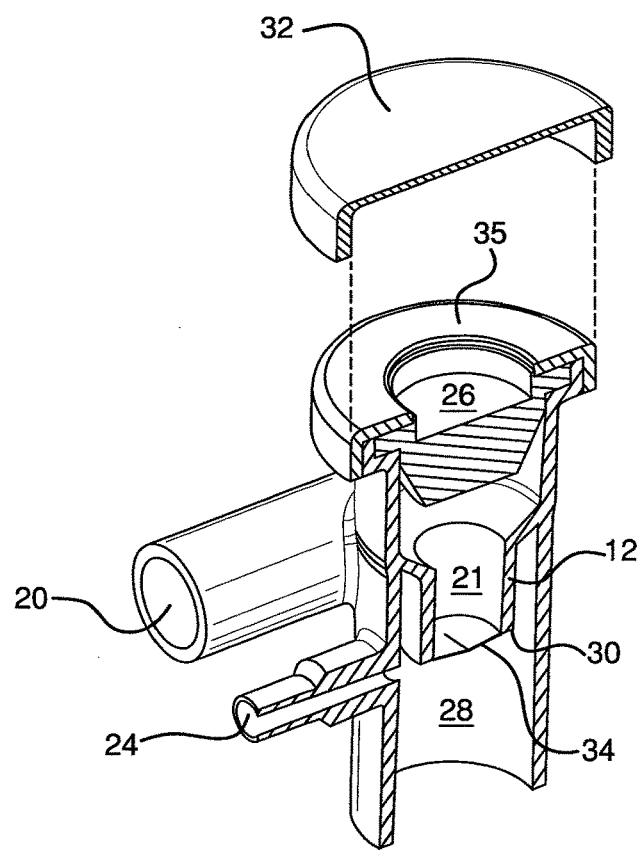
FIG. 4 is another isometric section view of another portion of the adaptor of FIG. 1A.

FIGS. 2A-2D illustrate the embodiment of the adaptor shown in FIG. 1A in more detail. As seen in FIG. 2A, the ventilation gas flow chamber 18 is joined with an aerosol flow chamber 17 to form a combined body 15 which houses a chamber 28 (as illustrated in FIGS. 2B, 2C, and 4). The aerosol flow channel 12 is nested within the chamber 28. As shown in FIG. 2B, the aerosol 21 is introduced into the aerosol flow channel 12 via aerosol inlet port 14, through valve 26. The aerosol 21 flows through the aerosol flow channel 12 to and through the aerosol outlet port 30, then to and through the patient interface port 16. The length L1 of the aerosol flow channel 12 is sufficient to extend beyond the ventilation gas flow chamber 18, but is recessed within the chamber 28 by a length L2 to minimize resistance arising from the patient's exhalations. The inventors have discovered that selecting the proper value for L1 has a direct impact on the volume of ventilation gas which reaches the patient interface port. Ventilation gas 23 is introduced through gas inlet port 20 into a ventilation gas flow channel 19 (shown in FIG. 2D) and follows a flow path that partially encircles the aerosol flow channel 12, but may be pulled toward the patient interface port 16 under certain circumstances (e.g., when aerosol flow is not being generated or when the aerosol flow rate is less than the patient's inspiratory flow (PIF) as indicated by "broken lines" in FIGS. 2B and 2C). As shown in FIG. 2B, the aerosol flow channel 12 occupies the entire volume of the aerosol flow chamber 17 at the portion near the aerosol inlet port 14 and above the ventilation gas flow chamber 18, then narrows between the ventilation gas flow chamber 18 and the aerosol outlet port 30 and thus creating a separation barrier between the aerosol flow and the ventilator flow, to enable the ventilation gas flow chamber 18 to at least partially encircle the aerosol flow channel 12. The separation barrier between the aerosol flow and the ventilator flow has a predetermined length L1. The inventors have discovered that introducing the aerosol to the chamber 28 at a point below the ventilation gas flow channel prevents high ventilatory flow rates from diluting the aerosol or at least decreases the aerosol dilution effect, thus allowing more of the aerosol to reach the patient interface. In order to maximize aerosol inhaled dose and decrease aerosol losses, the aerosol flow is selected to match the PIF. Nevertheless, ventilator flow rates are always significantly higher than PIF. Thus, by separation of aerosol flow from higher ventilator flows, aerosol dilution, which occurs whenever aerosol flow is introduced directly to the ventilatory flow path, can be avoided or minimized. Using the adaptor of the invention, the amount of the ventilation gas delivered to the patient can be regulated by selecting the length of the aerosol flow channel and/or regulating the pressure created by an increased demand for air which is not matched by the aerosol flow (e.g., when PIF is higher than the aerosol flow rate).

As shown in FIG. 2B, the aerosol flow channel 12 forms a funnel-like shape. This arrangement minimizes corners, and thus helps to prevent the accumulation of deposits within the adaptor. In an alternative embodiment shown in FIG. 2C, the aerosol flow channel 12 is substantially the same diameter throughout its length, and is not configured as a funnel. In either embodiment, the aerosol flow channel 12 is sufficiently narrower than the chamber 28 to allow for flow of ventilation gas 23 around the aerosol flow channel 12.

Figure 2D:
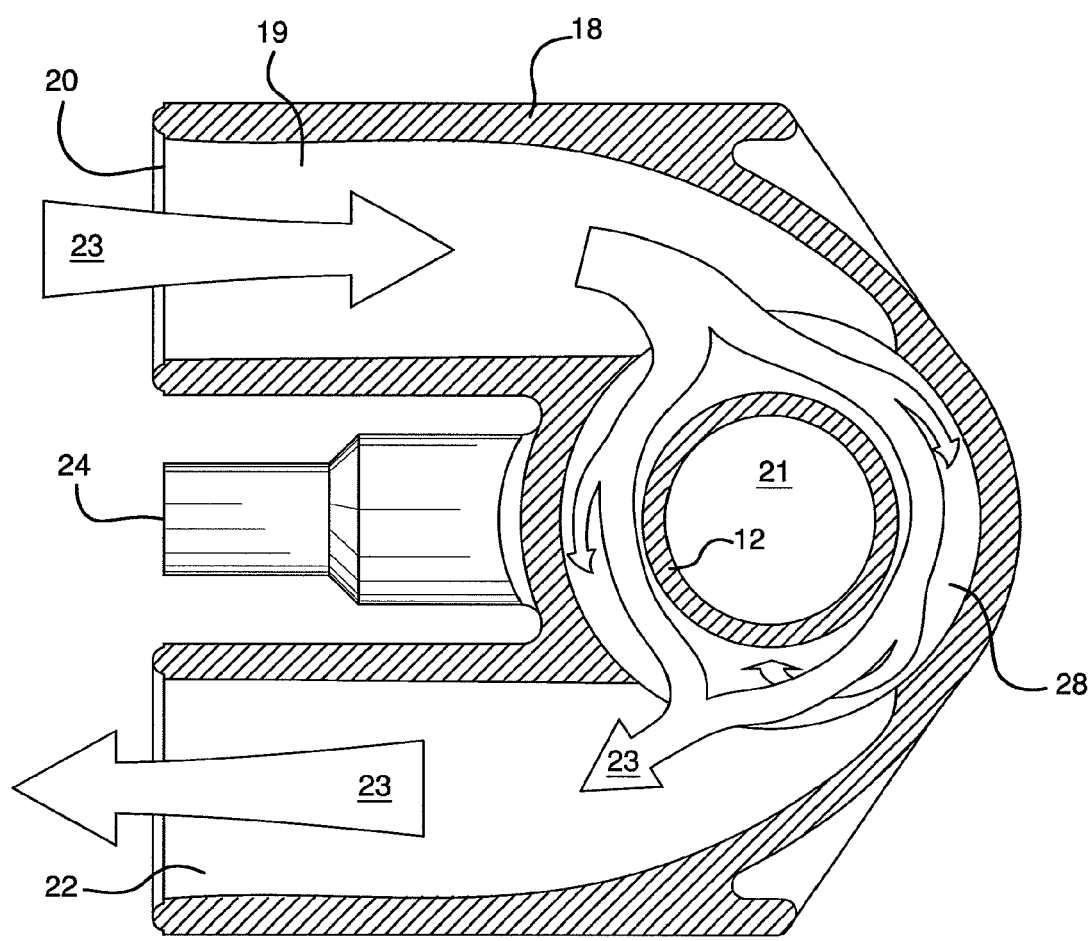
FIG. 2D is a section view of the adaptor of FIG. 2A, as seen along line 2D-2D.
Figure 3:
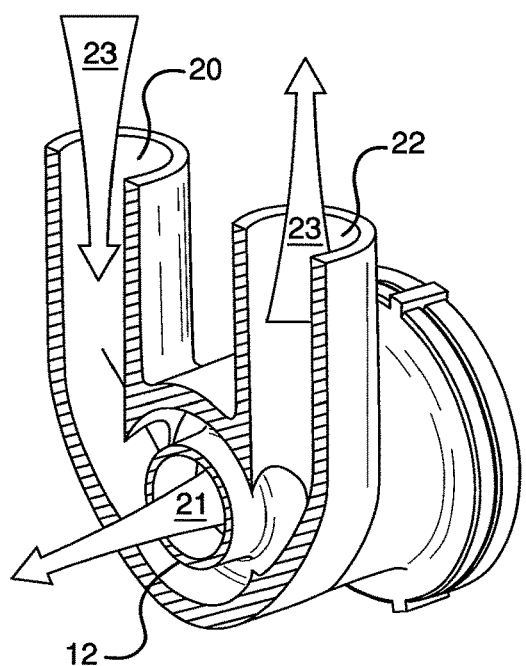
FIG. 3 is an isometric section view of a portion of the adaptor of FIG. 1A.

FIGS. 2D and 3 show the arrangement of the ventilation gas inlet and outlet ports 20/22 and the optional pressure sensor port 24, and the flow of ventilation gas around the aerosol flow channel 12. Ventilation gas flows into the ventilation gas flow channel 19 through port 20 and out through port 22, with a portion being pulled toward the patient interface port 16 through the chamber 28, substantially parallel to the aerosol flow path 21, under certain circumstances (e.g., when aerosol flow is not being generated or when the aerosol flow rate is less than the patient's inspiratory flow).

FIG. 4 illustrates the arrangement of the aerosol inlet port at the top of the adaptor. A removable cap 32 is shown. The cap 32 may be utilized when the aerosol generator is not being used, and removed when the adaptor is connected to an aerosol generator. The aerosol flows through valve 26 into the aerosol flow channel 12. The valve 26 is preferably a slit or cross-slit valve of the type known in the art. When an aerosol generator is attached to the adaptor, the valve 26 is forced into an open position. When the aerosol generator is removed, the valve 26 closes. The adaptor 10 may further comprise a one-way valve 34 at the aerosol outlet port 30, to reduce or prevent any reverse aerosol flows that might occur during excessive expirations. A security lock 35 is used to prevent dislocation of valve 26.

Figure 5A:
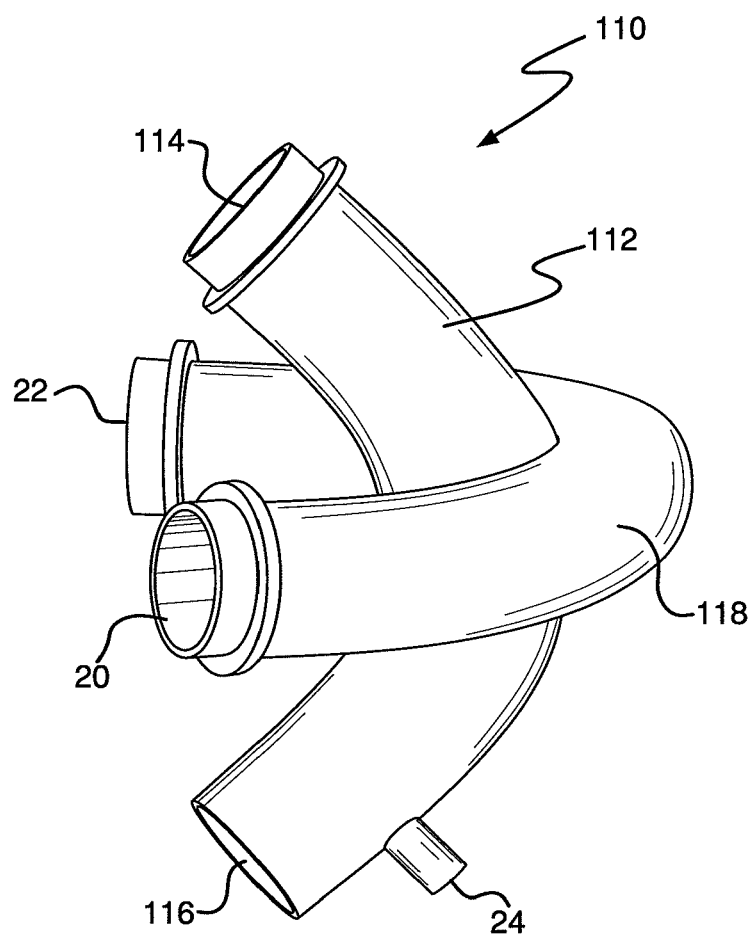
FIG. 5A is an isometric view of another embodiment of the adaptor of the present invention.

FIG. 5A shows another embodiment of the ventilation circuit adaptor 110, which includes an aerosol flow channel 112 and a ventilation gas flow channel 118. Similarly to the adaptor shown in FIGS. 1A-4, the aerosol flow channel 112 comprises an aerosol inlet port 114 with an optional valve (not visible) and a patient interface port 116. The ventilation gas flow channel 118 comprises ventilation gas inlet and outlet ports 20 and 22, respectively. In this embodiment, the ventilation gas flow channel is not adapted to form a chamber through which passes the aerosol flow channel. Instead, the aerosol flow channel 112 and the ventilation gas flow channel 118 are formed as substantially separated tubes, in fluid communication by means of an aperture 36 (shown in FIG. 7). In the embodiment shown, the optional pressure sensor port 24 is placed in the aerosol flow channel 112, near the patient interface. While the two flow channels are roughly tubular in shape, it will be appreciated by one of skill in the art that either or both channels may be of any cross-sectional dimension.

Figure 5C:
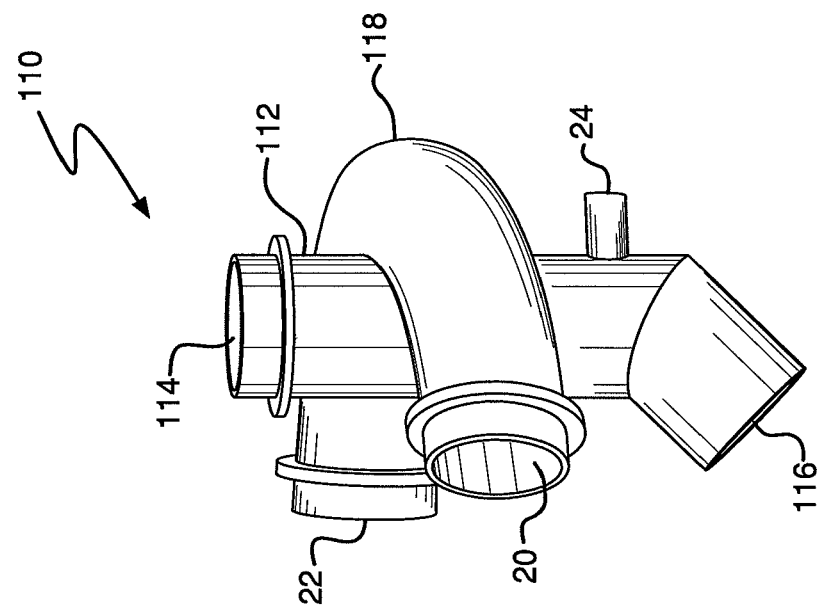
FIGS. 5B and 5C are isometric views of alternative embodiments of the adaptor.
Figure 5B:
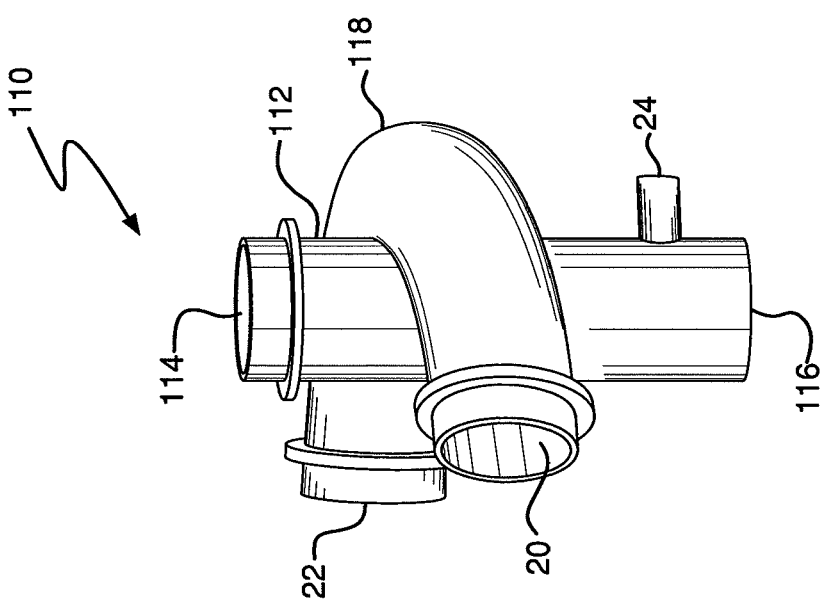

FIGS. 5B and 5C illustrate alternative embodiments of the adaptor shown in FIG. 5A. FIG. 5B shows a straight configuration for the aerosol flow channel 112; FIG. 5C shows an angled configuration for the aerosol flow channel 112.

Figure 6:
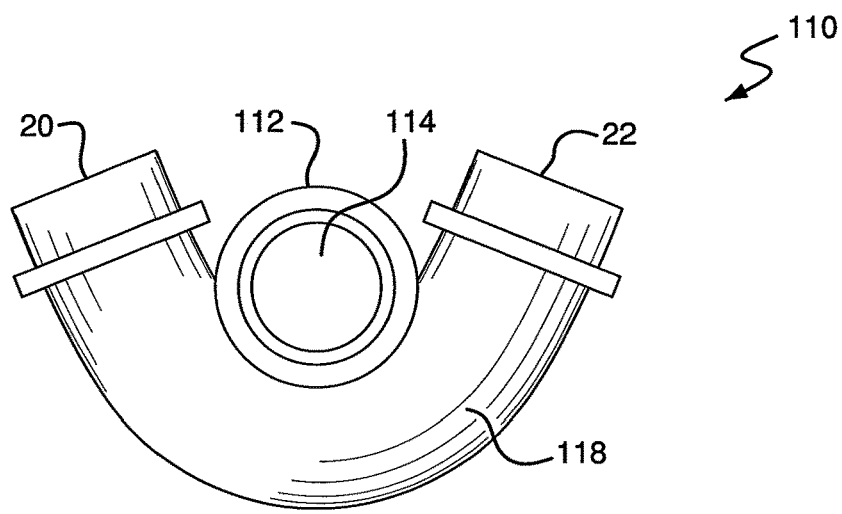
FIG. 6 is a top view of the adaptor shown in FIG. 5B.
Figure 7:
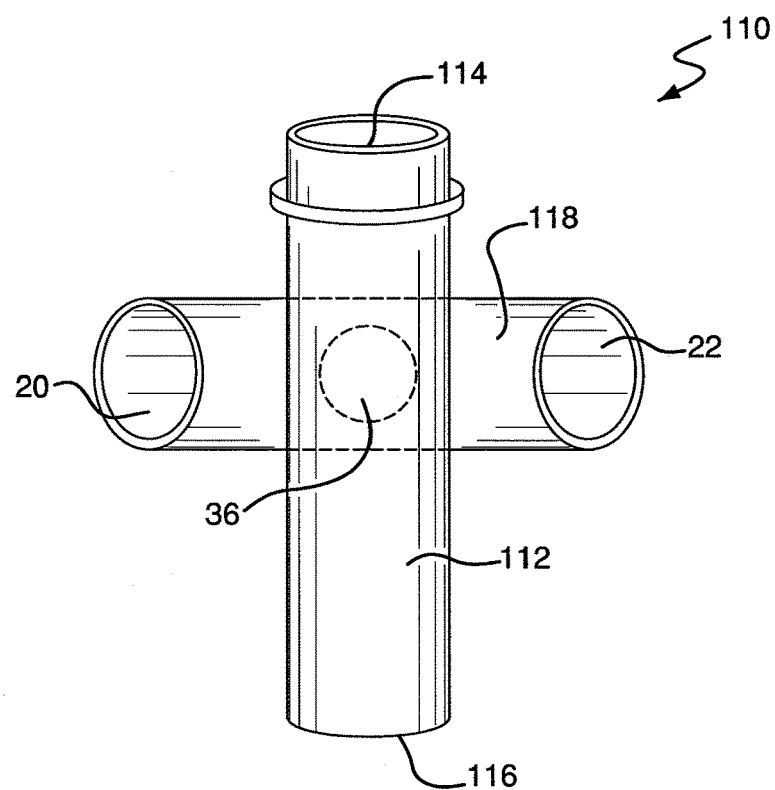
FIG. 7 is a plan view of the front of the adaptor of FIG. 5B.

FIG. 6 and FIG. 7 illustrate the embodiment of the adaptor shown in FIG. 5B viewed from different angles. As seen in the top view of FIG. 6 and the front view of FIG. 7, the ventilation gas flow channel 118 is substantially separated from the aerosol flow channel 112, and is in fluid communication therewith by means of an aperture 36. Aerosol is introduced into the aerosol flow channel 112 via aerosol inlet port 114, through optional valve 126 (not shown). The aerosol flows through the aerosol flow channel 112 to and through the patient interface port 116. Ventilation gas is introduced through gas inlet port 20 and follows a flow path that partially encircles the aerosol flow channel and exits at gas outlet port 22, but may move through the aperture 36 into the aerosol flow channel 112, toward the patient interface port 116 under certain circumstances (e.g., when aerosol flow is not being generated or when the aerosol flow rate is less than the patient's inspiratory flow).

Figure 8:
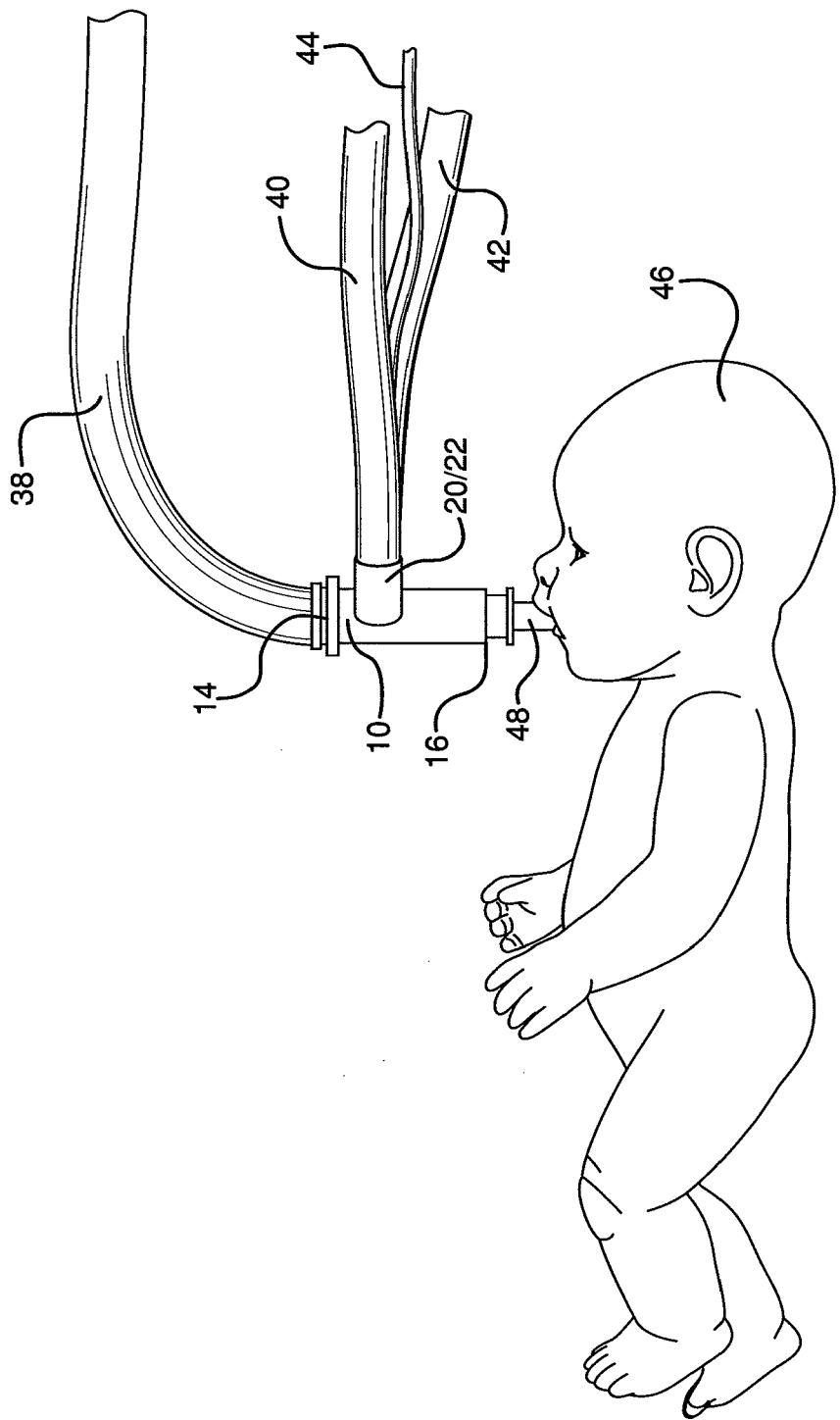
FIG. 8 illustrates a ventilatory circuit including an adaptor of the type shown in FIG. 1A, 1B, or 1C.

FIG. 8 depicts the arrangement of the adaptor 10 and various ventilatory and aerosol tubes of a system of the invention, as it may be used in a neonatal setting. It is understood that the adaptor can be used in any setting or with any apparatus suitable for pulmonary aerosol delivery. Tube 38 from the aerosol generator (generator not shown) is attached to the aerosol inlet port 14 of the adaptor 10. Ventilation gas inlet port 20 and outlet port 22 are affixed, respectively to tubes 40 and 42, which form the ventilatory circuit that includes the positive pressure generator (not shown). The pressure sensor port 24 (not shown) is attached via tubing 44 to a pressure sensor (pressure sensor not shown). The patient 46 is administered respiratory therapy through a patient interface, such as, for example, an endotracheal tube 48 which is affixed to the patient interface port 16.

The ventilation circuit adaptor of the present invention may be formed of, for example, polycarbonate or any other suitable material; however, materials such as molded plastic and the like, of a type used for tubing connectors in typical ventilatory circuits, are particularly suitable. The material utilized should be amenable to sterilization by one or more standard means. In certain embodiments, the adaptor is made of disposable materials. In certain embodiments, the adaptor is made of materials capable of withstanding temperatures and pressures suitable for sterilizing.

The adaptor may be of any size or shape within the functional parameters set forth herein. In a preferred embodiment, the adaptor is of a size and shape that enables its use with standard tubing and equipment used in mechanical ventilation circuits. This is of particular advantage over certain previously disclosed connectors (e.g., U.S. patent publication 2006/0120968 to Niven et al.), wherein the size of the chamber accounts for significant ventilation dead space, minimizing its effective use in invasive mechanical ventilation applications or other connectors (e.g., U.S. Pat. No. 7,201,167 to Fink et al.), wherein the aerosol is diluted with the ventilation gas. In particular embodiments, the adaptor is designed to replace the typical "Y" or "T" connector used in ventilatory circuits, and its size is such that no additional ventilation dead space is introduced into the ventilatory circuit. However, custom sizes and shapes may easily be fabricated to accommodate custom devices or equipment, as needed.

The ventilation circuit adaptor can comprise one or more optional features, either singly or in combination. These include: (1) one or more ports for attaching monitoring equipment, such as a pressure sensor; (2) a valve at the aerosol inlet port; (3) a removable cap for the aerosol inlet port; (4) a one-way valve at the aerosol outlet port; and (5) a temperature probe.

The port(s) for attaching monitoring equipment can be placed in various positions on the adaptor, as dictated by use with standard or custom equipment and in keeping with the intended function of the port. For instance, a pressure sensor port should be positioned on the adaptor such that ventilation and/or aerosol flow pressure can be accurately measured.

The valve at the aerosol inlet port is a particularly useful optional feature of the adaptor. Particularly suitable valves include slit or cross-slit valves. The valve is forced into an open position by attachment of an aerosol generator tube or the aerosol generator itself, and returns to a closed position when the aerosol generator tube is disconnected. As would be readily appreciated by the skilled artisan, the valve should be fabricated of material that is sufficiently flexible and resilient to enable to valve to return to a substantially closed, sealed position when the aerosol generator is disconnected. Thus, the valve at the aerosol inlet port enables a substantially constant pressure to be maintained within the ventilatory circuit even when the aerosol generator is not attached to the adaptor. Advantageously, the presence of the valve and resultant ability to maintain substantially constant positive pressure, enables the adaptor to serve as a point of access, allowing safe application of catheters or surgical and diagnostic devices such as fiberoptic scopes to patients under ventilatory support, without interrupting such breathing support. The catheters may be cleaning catheters used to clean the upper or lower airways, nebulizing catheters to deliver aerosolized drugs as well as other substances or conduits to deliver liquid drugs as well as other substances to the airways. The adaptor can also include a removable cap to seal the aerosol inlet port when the port is not in use.

In certain embodiments, the adaptor can further include a one-way valve at the aerosol outlet port. The one-way valve can be fabricated of flexible, resilient material that may be the same or different from the material used to fabricate the valve at the aerosol inlet port. The one-way valve at the aerosol outlet port can be included to reduce or prevent any reverse aerosol flow that might occur during excessive expirations.

In certain embodiments, some of which are depicted in FIGS. 1A-4, the ventilation gas flow channel is adapted to form a chamber through which passes the aerosol flow channel. In such embodiments, the walls defining the aerosol flow channel extend beyond the ventilation gas flow channel as defined by the ventilation gas inlet and outlet ports. However, the length of the aerosol flow channel is also such that the aerosol outlet port is recessed from the patient interface port, so as to reduce the risk or incidence of expiratory resistance during controlled mechanical ventilation (CMV) or intermittent mechanical ventilation (IMV). In certain embodiments designed for neonatal use, the aerosol outlet port is recessed from the patient interface port by at least about 8 millimeters (L2, FIG. 2B), with the chamber volume in the recess being at least about 1.4 milliliters. In certain embodiments designed for older infants, children or adults, the aerosol outlet port can be further recessed from the patient interface port, e.g., by at least about 9, 10, 11, 12, 13, 14, 15 or 16 millimeters, with concomitantly increased chamber volume in the recess, e.g., at least about 1.5, 1.6, 1.7, 1.8, 1.9, 2.0, 2.1, 2.2, 2.3, 2.4, 2.5, 2.6, 2.7, 2.8, 2.9 or 3.0 milliliters.

The ventilatory circuit adaptor of the present invention can be made from any material suitable for the delivery of the substances described herein, e.g., polymers, metals, or composite materials. It is preferred that the materials are capable of being sterilized. The adaptors can be manufactured by methods known in the art, such as, for example, injection molding.

The ventilatory circuit adaptor of the present invention can be used in any ventilatory circuit to adapt it for use with an aerosol generator. The aerosol generator is introduced into the circuit via the adaptor. The aerosol generator may be directly or indirectly connected to the adaptor, e.g., via tubing, as would be understood by the skilled artisan. Any type of nebulizer or aerosol generator may be used. For instance, the aerosol generator can be an ultrasonic nebulizer or vibrating membrane nebulizer or vibrating screen nebulizer. Typically, jet nebulizers are not employed although the present methods can be adapted to all types of nebulizers or atomizers. In one embodiment, the aerosol generator is an Aeroneb® Professional Nebulizer (Aerogen Inc., Mountain View, Calif., USA). In another embodiment, the aerosol generator is a capillary aerosol generator, an example of which is a soft-mist generator by Philip Morris USA, Inc. Richmond, Va. (see U.S. Pat. Nos. 5,743,251 and 7,040,314; T. T. Nguyen, K. A. Cox, M. Parker and S. Pham (2003) Generation and Characterization of Soft-Mist Aerosols from Aqueous Formulations Using the Capillary Aerosol Generator, J. Aerosol Med. 16:189).

In certain embodiments, the adaptor can be used with a conduit inserted into the aerosol inlet port, through the aerosol flow channel and out the patient interface directly into the patient's nose (e.g., via nasal prongs or nasal tube) or mouth (e.g., via endotracheal tube) such that an active agent is provided in a liquid form or an aerosol form via the conduit.

The ventilation circuit further comprises a patient interface, which is selected to accommodate the type of ventilatory support to be administered. Invasive applications such as controlled, assisted or intermittent mandatory ventilation will utilize an endotracheal or tracheostomy tube as the patient interface. Non-invasive applications such as CPAP or BI-PAP may utilize nasal prongs or nasopharyngeal tubes, or a mask that covers the nose or both the nose and mouth, as the patient interface. In certain embodiments, the patient interface is connected directly to the adaptor. In other embodiments, a length of tubing may be introduced between the adaptor and the patient interface.

Thus, in practice, the system of the invention is utilized by establishing the patient on respiratory ventilation utilizing a circuit that includes the adaptor, introducing one or more active agents into the aerosol generator attached to the adaptor, and delivering to the patient through the adaptor a flow of the aerosolized active agent. The actual dosage of active agents will of course vary according to factors such as the extent of exposure and particular status of the subject (e.g., the subject's age, size, fitness, extent of symptoms, susceptibility factors, and the like). By "effective dose" herein is meant a dose that produces effects for which it is administered. The exact dose will be ascertainable by one skilled in the art using known techniques. In one exemplary embodiment, the effective dose of pulmonary surfactant for delivery to a patient by the present methods will be from about 2 mg/kg surfactant total phospholipid (TPL) to about 175 mg/kg surfactant TPL. The length of treatment time will also be ascertainable by one skilled in the art and will depend on dose administered and delivery rate of the active agent. For example, in embodiments wherein the delivery rate of aerosol to a patient is about 0.6 mg/min, greater than 100 mg of aerosol can be delivered in less than a 3 hour time frame. It will be understood by the skilled practitioner that a lower delivery rate will correspond to longer administration times and a higher delivery rate will correspond to shorter times. Similarly, a change in dose will affect treatment time.

Another aspect of the invention is an improvement in a method of delivery of an aerosolized active agent with concomitant positive pressure ventilation to a patient, wherein the improvement comprises diverting a portion of pressurized ventilation gas directed to the patient and combining it with a concentrated aerosolized active agent in a chamber and using the portion of the pressurized ventilation gas as a carrier (sheath) gas for delivery of the aerosolized active agent to the patient, thereby creating an auxiliary circuit for a carrier gas and aerosol delivery to a patient. It should be understood that the auxiliary circuit described in detail below can be used with any device or adaptor which enables delivery of a combination of a ventilation air and aerosol flows to a patient.

In yet another embodiment, the adaptor of the invention can be used in a novel aerosol delivery system. The combination of the adapter and the ventilation circuit described above creates a Proximal Aerosol Delivery System (PADS) 100 as exemplified in FIGS. 9-11. In the PADS, an auxiliary circuit is created for diverting a portion of the inspiratory ventilation flow to the aerosol entrainment chamber (AEC) to be used as a carrier or sheath gas for delivery of aerosolized active agent to the regulator. Advantageously, the AEC collects a concentrated aerosolized active agent which is then diluted with the sheath gas to the desired concentration. Thus, the sheath gas plays a dual role as a transporter and a diluent of the aerosolized active agent.

PADS 100 comprises an inspiratory arm 40 equipped with a T-connector 39. The T-connector 39 allows directing a predetermined portion of the flow from the ventilation circuit to the sheath gas tube 51. The amount of the ventilation air diverted to the sheath gas tube 51 is selected based on patient's PIF (2-5 L/min for newborns, 6-20 L/min for pediatric population and 20-30 L/min for adults). The sheath gas tube 51 has a flow restrictor 50. The sheath gas tube 51 with the flow restrictor 50 assures delivery of appropriate air flow to an aerosol entrainment chamber (AEC) 52. The sheath gas flow is equal to or higher than the patient's PIF and is regulated by a flow restrictor. The sheath gas flow is preferably within the range of 2-5 L/min for neonatal population and respectively higher for pediatric (e.g., 6-20 L/min) and adult populations (e.g., 20-60 L/min). In another variant, a built-in air flow regulator can be used in place of a flow restrictor for adjusting the sheath gas flow. In such case, the built-in air flow regulator is located in the AEC.

The sheath gas tube 51 can be connected to the inspiratory arm 40 of the ventilation circuit before or after a heater/humidifier (not shown). The placement of the sheath gas tube connector depends on the type of aerosol delivered to the patient. If the aerosol generated by the nebulizer is relatively dry and there is a risk for particles growth in the humidified environment, the sheath gas tube connector will be placed before the heater/humidifier. If the aerosol generated by the nebulizer is relatively wet and there is not a risk for additional particles growth in the humidified environment, the sheath gas connector can be placed after the heater/humidifier.

The inspiratory arm 40 is adapted to deliver the balance of the ventilation flow 23 to the adaptor 10 via the inspiratory flow port 20 as described above.

PADS 100 also comprises an expiratory arm 42 equipped with an exhalation filter (not shown). The exhalation filter has satisfactory capacity in order to prevent aerosol from reaching a PEEP valve and/or ambient air in the 'bubble CPAP' circuit set-up. The expiratory arm 42 is connected with the adaptor 10 via the expiratory flow port 22 and is adapted to remove ventilation air flow 23 from the adaptor 10.

The adaptor 10 (or 110) is connected to the inspiratory arm 40, and the expiratory arm 42 via inspiratory flow port 20 and expiratory flow port 22 respectively. The adaptor assures appropriate separation of ventilator flows directing undiluted aerosol towards patient.

The purpose of the AEC 52 is to provide maximal aerosol entrainment and high aerosol concentration to the adaptor 10. The AEC 52 may have a built-in flow regulator for sheath gas flow adjustment.

An aerosol generator 55 is located proximate to or connected with the AEC 52. It should be understood that any type of aerosol generator including, for example, mesh vibrating, jet or capillary aerosol generators, can be used in this invention.

Figure 10:
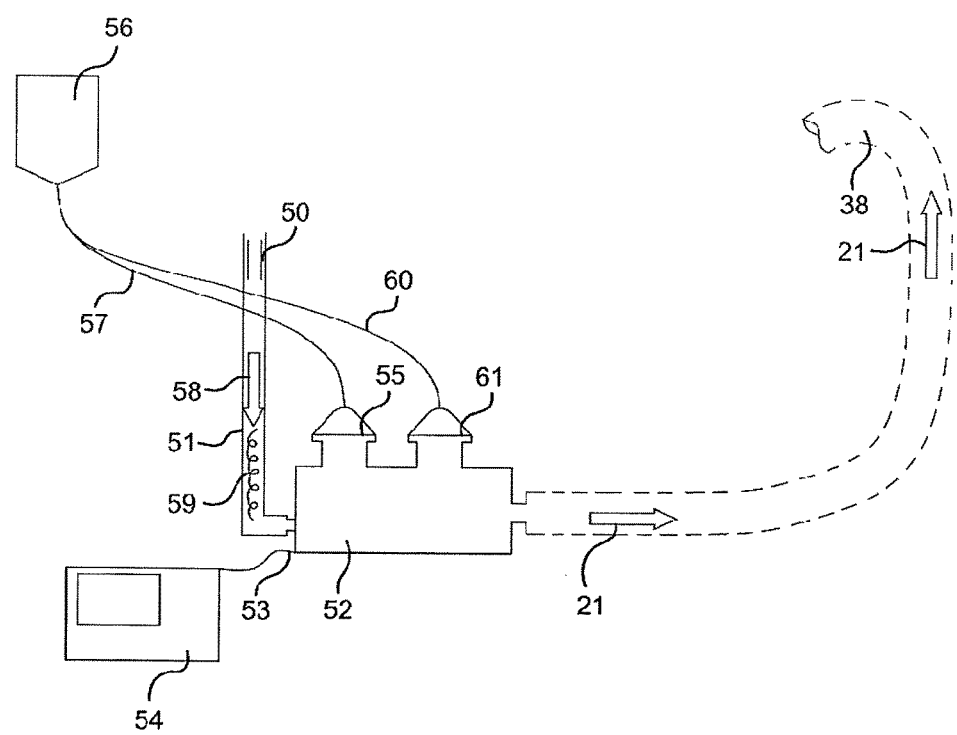
FIG. 10 a schematic diagram illustrating another embodiment of a proximal aerosol delivery system (PADS) suitable for delivery of multiple substances.

A drug reservoir 56 is connected with the aerosol generator 55 by means of a drug feeding line 57. The drug reservoir 56 and the feeding line assure drug supply to the aerosol generator, whenever nebulization is required including continuous supply. It should be understood that multiple drug reservoirs containing different drugs or reservoirs containing auxiliary substances other than drugs, e.g., pharmaceutically acceptable carriers together with multiple feeding lines, can be provided as needed (see, for example FIG. 11). Also, multiple aerosol generators can be used. An exemplary embodiment of such multiple aerosol generators is shown in FIG. 10, wherein a first aerosol generator 55 and a second aerosol generator 61 are connected to a drug reservoir 56 via first drug feeding line 57 and a second drug feeding line 60 respectively. In certain embodiments, the feeding line is eliminated and the drug reservoir is connected directly with the aerosol generator.

Figure 9:
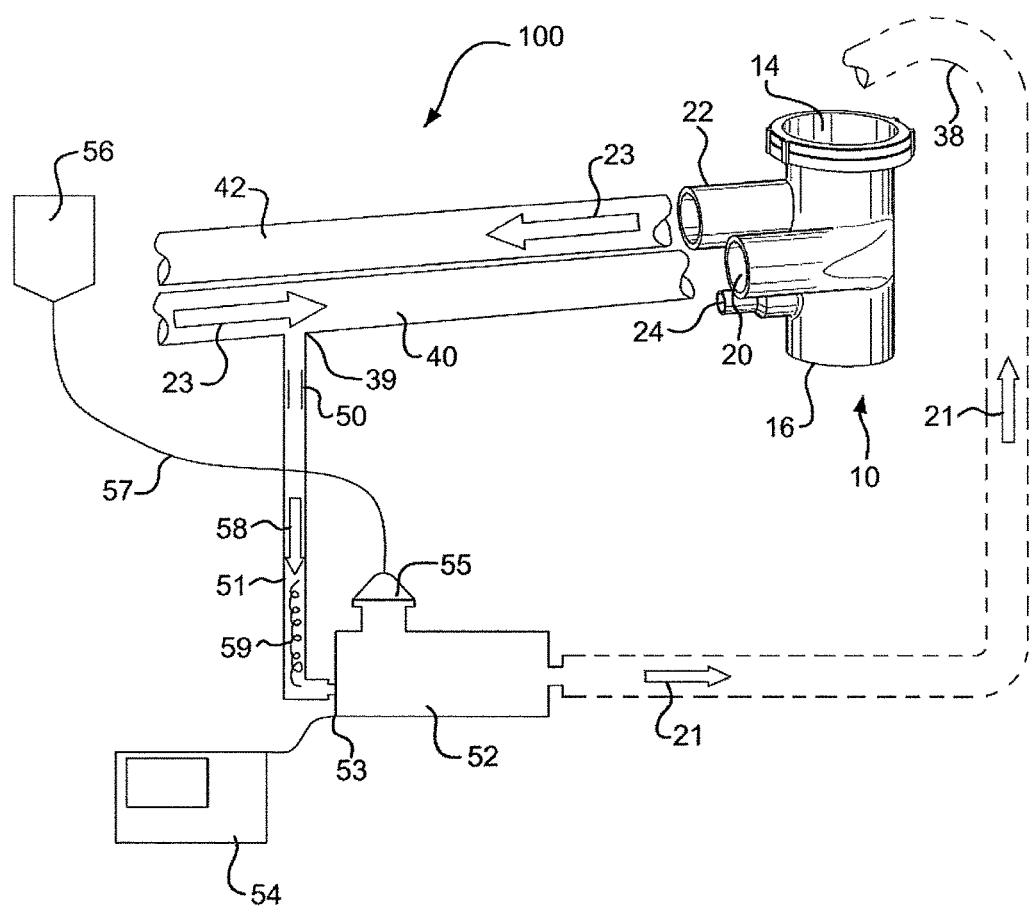
FIG. 9 is a schematic diagram illustrating a proximal aerosol delivery system (PADS).

A heating device 59 as shown in FIGS. 9 and 10 is located within the sheath gas tube 51 and is used to heat the sheath gas 58 flowing though the sheath gas tube 51 before the entrance to the AEC 52. The heating device is optional. It can be used for delivery of a heated air/aerosol mixture to a patient. Heating of the sheath gas can also decrease potential particle growth as the sheath gas is not humidified.

Figure 11:
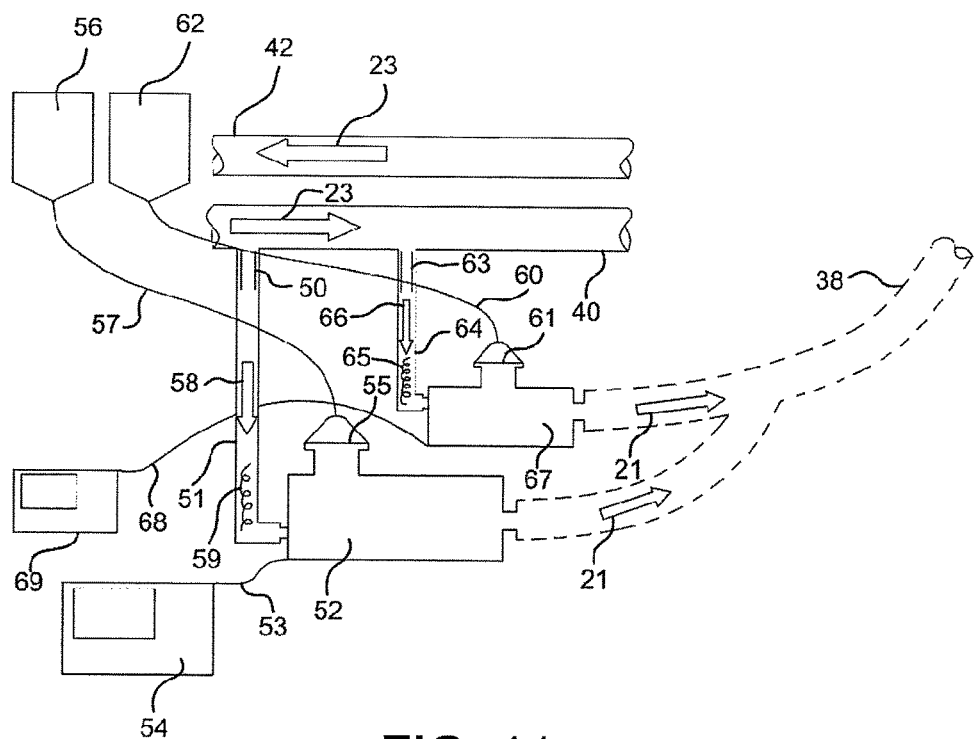
FIG. 11 a schematic diagram illustrating another embodiment of a proximal aerosol delivery system (PADS) suitable for delivery of multiple substances.

As shown in FIG. 11, two drug reservoirs 56 and 62 are connected via drug feeding lines 57 and 60 to respective Aerosol Entrainment Chambers 52 and 67. The auxiliary circuits are formed via two T-connectors and flow restrictors 50 and 63 allowing diverting a portion of the inspiratory ventilation gas into sheath gas tubes 51 and 64 to a respective AEC 52 and 67 for contacting with the aerosolized drug. Connecting conduits 53 and 68 are connecting each AEC with a corresponding control unit 54 and 69, wherein each control unit can have a free standing or a built-in patient interface. Heating devices 59 and 65 are located within the sheath gas tube 51 and 64 respectively. The aerosol flow 21 is combined at a junction located in the aerosol tube 38.

AECs and drug reservoirs can be made of polycarbonate or materials known in the art suitable for operating at temperatures and pressures in the range of 18-40C.° and 5-60 cm $H_2O$.

An aerosol tube 38 is adopted to carry an entrained aerosol 21 from the AEC 52 to the aerosol inlet port 14. The length of the aerosol tube 38 can be selected to achieve optimal delivery based on the type of aerosol and characteristics of aerosol generators as known in the art. In certain embodiments, the AEC 52 is connected directly with the port 14 without the aerosol tube 38. Any known connector proving an appropriate seal can be used for this purpose In certain embodiments, the length of aerosol tube 38 does not exceed 20 cm. Preferably, the aerosol tube 38 is expandable to secure the optimized placement of the nebulizer, for example, as close to the patient as possible but in comfortable location to avoid restriction of any nursing procedures and allow patient for some head motion. Expandable tubes will help avoid sharp angle creation and thus avoid potential aerosol deposition within the delivery system.

The aerosol tube can be equipped with an optional expandable aerosol reservoir (not shown). This reservoir is a balloon with a volume equal to or as close as possible to a patient's tidal volume and with compliance equalizing PIF. During inspiration, the patient will be breathing in aerosol without diluting it as described above, whereas during exhalation the balloon will refill with aerosol up to the volume of tidal volume or similar and thus limit the aerosol losses to the expiratory arm of the circuit. The resistance of the balloon will maintain desired pressure within the ventilator system. During the phase following inspiration, the patient will inhale optimized highly concentrated aerosol from the balloon as it will be pushed away by elastic forces. This system will limit losses of the drug during exhalation. The size of the balloon depends on the patient's tidal volume and can differ for particular age groups.

A control unit 54 is located outside a patient bed (not shown). The control unit 54 has a user interface allowing for input/output of relevant information, e.g., patient weight. Any suitable control unit can be used in this invention. A patient's weight determines PIF which is matched with sheath gas flow. The control unit 54 is in communication with the aerosol generator 55 and the AEC 52 through a wire 53 or wirelessly (e.g., bluetooth technology).

Advantages of PADS as compared to the existing aerosol delivery models include (a) eliminates aerosol dilution by high ventilator gas flows within ventilator circuits, (b) eliminates additional sources for sheath gas flow or aerosol flow, and (c) proximal placement to a patient interface and thus reduction of potential drug losses within the PADS. Moreover, none of the PADS components increase dead space. Distant location of the control unit makes device operations much easier.

PADS can be used with different modes of ventilation including but not limiting to CPAP, IMV, and synchronized intermittent mechanical ventilation (SIMV). A simple version of PADS without a built-in flow regulator can operate on IMV/SIMV mode based on this same relative increase of the sheath gas flow through AEC driven by the increased flow or pressure within the ventilation circuit. Thus, the increased sheath gas flow will deliver more aerosol through the adaptor towards the patient during inhalation. A more complex version of PADS with a built-in flow generator will increase the flow of sheath gas based on a mechanism triggered by a patient. Such triggering mechanism can be based, for example, on Grasbay capsule sensing diaphragm motion or Electric Activity of the Diaphragm (EAdi) [12] which is clinically known as Neuronal Adjusted Ventilation (NAVA) sensing the phrenic and diaphragm nerve impulses. In such case the signals can be analyzed in a microprocessor controlling the flow meter within the AEC and sheath gas flow can be adjusted accordingly. In both scenarios described above, the nebulizer is operating continuously generating aerosol all the time. The aerosol generator can also be controlled based on the patient triggering mechanism. Again, the impulses based on NAVA technology could activate generation of aerosol before a patient is starting inspiration due to signal analysis by the microprocessor built in within AEC. The aerosol generator activation can be supported with the increased sheath gas flow as described above. The end of inspiration as well as aerosol generation can be determined based on the strength of the neuronal signal as described by NAVA.

The invention will be illustrated in more detail with reference to the following Examples, but it should be understood that the present invention is not deemed to be limited thereto.

EXAMPLES

Example 1

Oxygen Dilution by Different Adaptor Designs

This protocol was designed to characterize the aerosol dilution effect of three different ventilation circuit adaptor adaptors for use with CPAP: a) the adaptor as described by U.S. patent publication 2006/0120968 to Niven et al. (adaptor 1); b) a 'high resistant adaptor' (adaptor 2 as shown in FIGS. 1A, 2A-4, 10 mm aerosol flow tube (L1 in FIG. 2B)); and c) a 'low resistant adaptor' (adaptor 3 as shown in FIGS. 1A, 2A-4, 5-6 mm aerosol flow tube (L1 in FIG. 2B)). In order to measure the dilution of aerosol, gases with two different concentrations of oxygen were used: 100% oxygen gas for aerosol flow and 21% oxygen gas for CPAP flow. The adaptors were tested under different CPAP flow conditions (6, 8, 10 and 12 L/min), and different steady state, potential inspiratory flows (0.3, 1.04, 3.22 and 5.18 L/min). The aerosol flow was constant at 3 L/min, the CPAP pressure maintained at 5 cm $H_2O$ for all tested conditions.

The CPAP ventilation circuit was based on the Infant Star additional blended gas source with a flow meter. One end of the inspiratory limb of the circuit was connected to the blended gas flow meter and the other end to the inspiratory port of the tested ventilation circuit adaptor. The expiratory limb of the circuit was connected to the expiratory port of adaptor and the other end to a 5 cm $H_2O$ PEEP valve. The ET tube port of the tested adaptor was connected to a rotameter through a 'T' connector. The oxymeter was connected to the circuit via this 'T' connector. A pressure manometer was connected to the adaptor via the pressure monitoring port. The oxymeter and pressure manometer were calibrated prior the initiation of the experiment. The oxygen tube was connected to the flow meter of the oxygen source and the other end to the aerosol port of the adaptor mimicking the aerosol flow. There were 5 recordings of every measurement done, 10 seconds apart. Collected data represent the oxygen concentration, and are presented as dilution factor value calculated using the equation:

$$Y = x - 21\%/79\%$$

The results are presented as dilution factor values in Table 1. Both the adaptor 1 and the adaptor 2 (high resistance adaptor) showed no relationship between the different CPAP flows and the different inspiratory flows, i.e., no dilution was observed at any tested combination. Whenever inspiratory flow exceeded aerosol flow (i.e., was larger than approximately 3 L/min), a dilution effect was observed, as was expected. The adaptor 2 demonstrated somewhat better results for the condition when inspiratory flow was equal to aerosol flow. The adaptor 3 (low resistant CPAP adaptor) did not perform as well as the other two adaptors. A significant dilution effect was observed with CPAP flows higher than 4 L/min in the adaptor 3. The greatest dilution effect was noted for a CPAP flow of 12 L/min with a 0.8 dilution effect, compared to almost no dilution with the other two adaptors.

Overall, the design of the adaptors 2 and 3 is much different than the design of the adaptor 1. The inner volumes of both adaptors 2 and 3 are similar to the inner volume of the standard 'Y' connector, which allows for much safer use in combination with any type of breathing support. These adaptors can be used interchangeably for aerosol delivery under different ventilatory support conditions or just for ventilation during interim periods in aerosol therapy.

In summary, in this study, the adaptor 2 was superior in comparison to other two tested adaptors in introducing and directing undiluted oxygen towards the patient's interface due to the selection of L1.

TABLE 1

| Insp Flow | Prior Art Adaptor-Adaptor1 CPAP Flow L/min | | | | | High Res. Adaptor-Adaptor2 CPAP Flow L/min | | | | | Low Res. Adaptor-Adaptor 3 CPAP Flow L/min | | | | |
|---|---|---|---|---|---|---|---|---|---|---|---|---|---|---|---|
| 0.3 L/min | 4 | 6 | 8 | 10 | 12 | 4 | 6 | 8 | 10 | 12 | 4 | 6 | 8 | 10 | 12 |
| #1 | 1 | 0.98734 | 0.98734 | 0.9747 | 0.98734 | 0.9873 | 1 | 1 | 0.98734 | 0.98734 | 0.98734 | 0.94937 | 0.92405 | 0.86076 | 0.79747 |
| #2 | 1 | 1 | 0.97468 | 0.9873 | 0.98734 | 1 | 1.01266 | 1 | 1 | 0.98734 | 0.98734 | 0.94937 | 0.89873 | 0.86076 | 0.79747 |
| #3 | 1 | 0.98734 | 0.98734 | 0.9873 | 0.98734 | 0.9873 | 1 | 1 | 0.98734 | 0.98734 | 0.98734 | 0.94937 | 0.89873 | 0.86076 | 0.79747 |
| #4 | 1 | 1 | 0.97468 | 0.9873 | 0.98734 | 0.9873 | 1 | 1 | 0.98734 | 0.98734 | 0.98734 | 0.93671 | 0.91139 | 0.86076 | 0.79747 |
| #5 | 0.987342 | 1 | 0.98734 | 0.9873 | 0.98734 | 0.9873 | 1 | 0.98734 | 0.98734 | 0.98734 | 0.98734 | 0.94937 | 0.88608 | 0.8481 | 0.78481 |
| mean | 0.997468 | 0.99494 | 0.98228 | 0.9848 | 0.98734 | 0.9899 | 1.00253 | 0.99747 | 0.99241 | 0.99241 | 0.98734 | 0.94684 | 0.9038 | 0.85823 | 0.79494 |
| SD | 0.005661 | 0.00693 | 0.00566 | 0.0057 | 1.2E-16 | 0.0057 | 0.00566 | 0.00566 | 0.00693 | 0.00693 | 1.2E-16 | 0.00566 | 0.01443 | 0.00566 | 0.00566 |
| Insp Flow 1.04 L/min | | | | | | | | | | | | | | | |
| #1 | 0.987342 | 0.97468 | 0.97468 | 0.9873 | 0.98734 | 0.9873 | 0.98734 | 0.97468 | 0.98734 | 0.97468 | 0.98734 | 0.96203 | 0.91139 | 0.8481 | 0.79747 |
| #2 | 0.987342 | 0.97468 | 0.97468 | 0.9873 | 0.98734 | 0.9747 | 0.98734 | 0.98734 | 0.98734 | 0.98734 | 0.97468 | 0.94937 | 0.89873 | 0.86076 | 0.79747 |
| #3 | 0.974684 | 0.96203 | 0.97468 | 0.9873 | 0.98734 | 0.9873 | 0.98734 | 0.98734 | 0.98734 | 0.98734 | 0.98734 | 0.96203 | 0.89873 | 0.86076 | 0.77215 |
| #4 | 0.974684 | 0.97468 | 0.97468 | 0.9873 | 0.98734 | 0.9747 | 0.98734 | 0.98734 | 0.98734 | 0.97468 | 0.98734 | 0.96203 | 0.91139 | 0.8481 | 0.79747 |
| #5 | 0.974684 | 0.97468 | 0.97468 | 0.9873 | 0.98734 | 0.9797 | 0.98734 | 0.98734 | 0.97468 | 0.98734 | 0.98228 | 0.95949 | 0.90633 | 0.8481 | 0.79241 |
| mean | 0.979747 | 0.97215 | 0.97722 | 0.9873 | 0.98734 | 0.9797 | 0.98734 | 0.98481 | 0.98481 | 0.98481 | 0.98228 | 0.95949 | 0.90633 | 0.85316 | 0.79241 |
| SD | 0.006933 | 0.00566 | 0.00566 | 1E-16 | 1.2E-16 | 0.0069 | 0.00693 | 0.00566 | 0.00566 | 0.00566 | 0.00693 | 0.00566 | 0.00693 | 0.00693 | 0.01132 |
| Insp Flow 3.22 L/min | | | | | | | | | | | | | | | |
| #1 | 0.936709 | 0.93671 | 0.9367 | 0.9367 | 0.92405 | 0.9873 | 0.98734 | 0.98734 | 0.98734 | 0.98734 | 0.94937 | 0.89873 | 0.83544 | 0.77215 | 0.68354 |
| #2 | 0.924051 | 0.94937 | 0.93671 | 0.9241 | 0.91139 | 0.9873 | 0.98734 | 0.98734 | 0.98734 | 0.97468 | 0.93671 | 0.88608 | 0.8481 | 0.78481 | 0.68354 |
| #3 | 0.936709 | 0.94937 | 0.93671 | 0.9367 | 0.91139 | 1 | 0.98734 | 0.98734 | 0.98734 | 0.97468 | 0.94937 | 0.88608 | 0.8481 | 0.77215 | 0.68354 |
| #4 | 0.924051 | 0.93671 | 0.92405 | 0.9367 | 0.92405 | 1 | 0.98734 | 0.98734 | 0.97468 | 0.97468 | 0.94937 | 0.88608 | 0.8481 | 0.77215 | 0.68354 |
| #5 | 0.931646 | 0.9443 | 0.93418 | 0.9241 | 0.91899 | 0.9949 | 0.98734 | 0.98987 | 0.98481 | 0.97975 | 0.94684 | 0.88861 | 0.84557 | 0.77468 | 0.6962 |
| mean | | | | | | | | | | | | | | | |
| SD | 0.006933 | 0.00693 | 0.00566 | 0.0069 | 0.00693 | 0.0069 | 1.2E-16 | 0.00566 | 0.00566 | 0.00693 | 0.00566 | 0.00566 | 0.00566 | 0.00566 | 0.00566 |
| Insp Flow 5.18 L/min | | | | | | | | | | | | | | | |
| #1 | 0.696203 | 0.67089 | 0.6962 | 0.6962 | 0.68354 | 0.5949 | 0.72152 | 0.78481 | 0.79747 | 0.78481 | 0.75949 | 0.70886 | 0.67089 | 0.62025 | 0.59494 |
| #2 | 0.696203 | 0.67089 | 0.6962 | 0.6835 | 0.68354 | 0.5949 | 0.72152 | 0.78481 | 0.81013 | 0.78481 | 0.75949 | 0.70886 | 0.67089 | 0.63291 | 0.58228 |
| #3 | 0.683544 | 0.6962 | 0.6962 | 0.6835 | 0.6962 | 0.6203 | 0.73418 | 0.77215 | 0.79747 | 0.78481 | 0.75949 | 0.88608 | 0.65823 | 0.62025 | 0.58228 |
| #4 | 0.696203 | 0.6962 | 0.68354 | 0.6835 | 0.68354 | 0.5949 | 0.73418 | 0.77215 | 0.81013 | 0.79747 | 0.74684 | 0.6962 | 0.65823 | 0.62025 | 0.58228 |
| #5 | 0.683544 | 0.68354 | 0.68354 | 0.6861 | 0.68608 | 0.5823 | 0.72911 | 0.77722 | 0.80506 | 0.78987 | 0.75443 | 0.7038 | 0.66329 | 0.62278 | 0.58481 |
| mean | 0.691139 | 0.68354 | 0.69114 | 0.6861 | 0.68608 | 0.5975 | 0.72911 | 0.77722 | 0.80506 | 0.78987 | 0.75443 | 0.7038 | 0.66329 | 0.62278 | 0.58481 |
| SD | 0.006933 | 0.01266 | 0.00693 | 0.0057 | 0.00566 | 0.0139 | 0.00693 | 0.00693 | 0.00693 | 0.00693 | 0.00693 | 0.00693 | 0.00693 | 0.00566 | 0.00566 |

Example 2

Resistance Measurements of Different Adaptor Designs

The purpose of this study was to evaluate the operational characteristics of different ventilation circuit adaptors used for aerosol introduction into the CPAP ventilation circuit at the level of a 'Y' connector. Operational characteristics were assessed based on the resistance values of different adaptors tested under typical ventilation conditions for the potential targeted neonatal population.

The protocol was designed to characterize the operational characteristics of three different ventilation circuit adaptors and a standard 'Y' connector under dynamic flow conditions as intermittent mechanical ventilation (IMV): a) the adaptor as described by US patent publication 2006/0120968 to Niven et al. (the adaptor 1); b) a 'high resistant CPAP adaptor' (the adaptor 2 as shown in FIGS. 1A, 2A-4, 10 mm aerosol flow tube); c) a 'low resistant adaptor' (the adaptor 3 as shown in FIGS. 1A, 2A-4, 5-6 mm aerosol flow tube); and d) a 'standard Y connector' (the adaptor 4). These CPAP adaptors were tested under two different inspiratory flow conditions (approximately 1 and 3 L/min respectively). The operational characteristics of different adaptors were based on resistance measurements performed by airway manometry and pneumotachography.

The ventilator circuit was based on the Harvard small animal ventilator. One end of the inspiratory limb of the circuit was connected to the inspiratory port of the ventilator and the other end to the inspiratory port of the tested ventilation circuit adaptor. The expiratory limb of the circuit was connected to the expiratory port of the adaptor and the other end to the expiratory port of the Harvard ventilator. A pressure manometer was connected to the adaptor via the pressure monitoring port. The pressure manometer was calibrated prior the initiation of the experiment. The aerosol port of the adaptor was securely closed. There was 1 recording for every measurement done based on the PEDS calculations from at least 10 breathing cycles. Data represent the mean and standard error of the mean (SEM) values of inspiratory, expiratory, and total resistance.

The results are presented as mean and SEM values for total, inspiratory and expiratory resistance in Table 2. None of the tested adaptors showed higher resistance values (within 10%) compared to the 'standard Y connector' (the adaptor 4), which served as a reference for this test. In fact, the 'high resistant adaptor' (the adaptor 2) had lower resistance values measured under two different inspiratory flow conditions than the 'standard Y connector'.

Example 3

Preclinical Study

A preclinical study on preterm lamb has been aimed on proving the efficacy of aerosolized lucinactant for inhalation for prevention of RDS, and has utilized an embodiment of the ventilatory circuit adaptor of the invention as shown in FIGS. 1A, 2A. Four preterm lambs with gestation age of 126-128 days were treated with CPAP after preterm delivery. Within 30 minutes after birth the aerosolized surfactant treatment was initiated. The adaptor has efficiently delivered aerosol to the animals without any noted adverse events.

While the invention has been described in detail and with reference to specific examples thereof, it will be apparent to one skilled in the art that various changes and modifications can be made therein without departing from the spirit and scope thereof.

REFERENCES

1. Kattwinkel, J., et al., *Technique for intrapartum administration of surfactant without requirement for an endotracheal tube*. J Perinatol, 2004. 24: p. 360-365.
2. Trevisanuto, D., et al., *Laryngeal mask airway used as a delivery conduit for the administration of surfactant to preterm infants with respiratory distress syndrome*. Biol Neonate, 2005. 87(4): p. 217-20.
3. Richardson, C. and A. Jung, *Effect of continuous positive airway pressure on pulmonary function and blood gases of infants with respiratory distress syndrome*. Pediatr Res, 1978. 12: p. 771-4.
4. Gaon, P., et al., *Assessment of effect of nasal continuous positive pressure on laryngeal opening using fibre optic laryngoscopy*. Arch Dis Child Fetal Neonatal Ed, 1999. 80(3): p. F230-2.
5. Thomson, M., et al., *Treatment of immature baboons for 28 days with early nasal continuous positive airway pressure*. Am J Respir Crit Care Med, 2004. 169(9): p. 1054-62.
6. Verder, H., et al., *Surfactant therapy and nasal continuous positive airway pressure for newborns with respiratory distress syndrome. Danish-Swedish Multicenter Study Group*. N Engl J Med, 1994. 331(16): p. 1051-5.
7. Verder, H., et al., *Nasal continuous positive airway pressure and early surfactant therapy for respiratory distress syndrome in newborns of less than 30 weeks' gestation*. Pediatrics, 1999. 103(2): p. E24.
8. Dolovich, M., *Influence of inspiratory flow rate, particle size, and airway caliber on aerosolized drug delivery to the lung*. Respir Care, 2000. 45(6): p. 597-608.
9. Becquemin, M., et al., *Particle deposition and resistance in the nose of adults and children*. Eur Respir J, 1991. 4: p. 694-702.

TABLE 2

| | PIF = 1.3-1.4 mL/min Resistance mL/cm H$_2$O | | | | | | PIF = 2.9-3.2 mL/min Resistance mL/cm H$_2$O | | | | | |
|---|---|---|---|---|---|---|---|---|---|---|---|---|
| | Inspiratory | | Expiratory | | Total | | Inspiratory | | Expiratory | | Total | |
| Adaptor | mean | SEM | mean | SEM | mean | SEM | mean | SEM | mean | SEM | Mean | SEM |
| #1 | 28.02 | 0.68 | 35.56 | 0.12 | 24.62 | 0.06 | 33.58 | 0.23 | 57 | 0.7 | 39.98 | 1.46 |
| #2 | 27.9 | 0.44 | 32.08 | 0.04 | 25.34 | 0.07 | 26 | 0.22 | 49.78 | 0.28 | 30.43 | 0.19 |
| #3 | 33.63 | 0.28 | 35.55 | 0.13 | 27.11 | 0.18 | 31.57 | 0.18 | 55.17 | 0.57 | 38.74 | 0.21 |
| #4 | 32.04 | 0.28 | 30.26 | 5.5 | 26.61 | 0.7 | 29.98 | 0.4 | 55.39 | 0.33 | 36.46 | 0.27 |

10. Salmon, B., N. Wilson, and M. Silverman, *How much aerosol reaches the lungs of wheezy infants and toddlers.* Arch Dis Child, 1989. 65: p. 401-403.
11. Fink, J. B., et al., *Can high efficiency aerosol delivery continue after extubation.* Crit Care, 2005. 9(Suppl 1): p. P129.
12. Beck, J., et al., *Prolonged neural expiratory time induced by mechanical ventilation in infants.* Pediatr Res, 2004. 55(5): p. 747-754.

What is claimed is:

1. An adaptor for delivering an aerosolized active agent or a gasified active agent to a patient with concomitant positive pressure ventilation, comprising:
   a) a patient interface port;
   b) an aerosol flow channel having an aerosol inlet port and an aerosol outlet port, wherein the aerosol flow channel has a length between the aerosol inlet port and the aerosol outlet port and wherein the aerosol flow channel is adapted to enclose an aerosol flow along the length of the aerosol flow channel; and
   c) a ventilation gas flow channel in fluid communication with the patient interface port and the aerosol outlet port and having a gas inlet port and a gas outlet port, and wherein the ventilation gas flow channel is separated from the aerosol flow channel and is at least partially offset from the aerosol outlet port and at least partially encircles the aerosol flow channel;
   wherein the ventilation gas flow channel forms a chamber that includes the gas inlet port, the gas outlet port and the patient interface port, wherein the aerosol flow channel is at least partially nested within the chamber and extends from the aerosol inlet port at one end of the chamber through the chamber to the aerosol outlet port within the chamber such that the aerosol outlet port is recessed from the patient interface port at the opposite end of the chamber, wherein the aerosol flow channel is of a sufficient length to extend below an entrance of a gas from the gas inlet port into the chamber and below an exit of the gas from the chamber into the gas outlet port.

2. The adaptor of claim 1, further comprising a valve at the aerosol inlet port.

3. The adaptor of claim 2, wherein the valve is sufficiently flexible to allow introduction of at least one of an instrument, a catheter, a tube, or a fiber into and through at least one of the aerosol flow channel and the patient interface port, while maintaining positive ventilatory pressure.

4. The adaptor of claim 1, wherein the aerosol flow channel defines a substantially straight aerosol flow path, a curved aerosol flow path, or an angled aerosol flow path.

5. The adaptor of claim 1, wherein the aerosol flow channel has a substantially uniform cross-sectional area.

6. The adaptor of claim 1, wherein the aerosol flow channel has a greater cross sectional area at the aerosol inlet port than at the patient interface port.

7. The adaptor of claim 1, wherein the aerosol outlet port is recessed from the patient interface port by at least about 8 millimeters.

8. The adaptor of claim 1, wherein the chamber has a volume between the aerosol outlet port and the patient interface port of at least about 1.4 milliliters.

9. The adaptor of claim 1, further comprising a one-way valve at the aerosol outlet port.

\* \* \* \* \*